United States Patent
Standke et al.

(10) Patent No.: US 9,296,766 B2
(45) Date of Patent: Mar. 29, 2016

(54) MIXTURES, PARTICULARLY LOW IN VOLATILE ORGANIC COMPOUNDS (VOC), OF OLEFINICALLY FUNCTIONALISED SILOXANE OLIGOMERS BASED O ALKOXY SILANES

(71) Applicants: Burkhard Standke, Loerrach (DE); Kerstin Weissenbach, Gengenbach (DE); Jaroslaw Monkiewicz, Rheinfelden (DE); Sven Roth, Schwoerstadt (DE); Bernd Nowitzki, Marl (DE); Manuel Friedel, Zurich (CH)

(72) Inventors: Burkhard Standke, Loerrach (DE); Kerstin Weissenbach, Gengenbach (DE); Jaroslaw Monkiewicz, Rheinfelden (DE); Sven Roth, Schwoerstadt (DE); Bernd Nowitzki, Marl (DE); Manuel Friedel, Zurich (CH)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/360,114

(22) PCT Filed: Nov. 19, 2012

(86) PCT No.: PCT/EP2012/072969
§ 371 (c)(1),
(2) Date: May 22, 2014

(87) PCT Pub. No.: WO2013/076035
PCT Pub. Date: May 30, 2013

(65) Prior Publication Data
US 2015/0080531 A1 Mar. 19, 2015

(30) Foreign Application Priority Data
Nov. 22, 2011 (DE) .......... 10 2011 086 863

(51) Int. Cl.
*C08G 77/20* (2006.01)
*C07F 7/18* (2006.01)
*C08G 77/04* (2006.01)
*C08L 83/04* (2006.01)
*C09D 183/04* (2006.01)
*C09J 183/04* (2006.01)

(52) U.S. Cl.
CPC .......... *C07F 7/1812* (2013.01); *C07F 7/1892* (2013.01); *C08G 77/045* (2013.01); *C08G 77/20* (2013.01); *C08L 83/04* (2013.01); *C09D 183/04* (2013.01); *C09J 183/04* (2013.01)

(58) Field of Classification Search
None
See application file for complete search history.

(56) References Cited

U.S. PATENT DOCUMENTS

| 4,985,342 A * | 1/1991 | Muramoto ............ G03F 7/0757 430/270.1 |
|---|---|---|
| 5,282,998 A | 2/1994 | Horn et al. |
| 5,885,341 A | 3/1999 | Standke et al. |
| 6,395,856 B1 | 5/2002 | Petty et al. |
| 6,767,982 B2 | 7/2004 | Standke et al. |
| 6,780,955 B2 | 8/2004 | Barfurth et al. |
| 6,864,323 B2 | 3/2005 | Schlosser et al. |
| 7,781,520 B2 | 8/2010 | Standke et al. |
| 8,236,918 B2 | 8/2012 | Mueh et al. |
| 8,431,646 B2 | 4/2013 | Giessler-Blank et al. |
| 8,795,784 B2 | 8/2014 | Standke et al. |
| 2003/0166817 A1 | 9/2003 | Barfurth et al. |
| 2006/0235179 A1 * | 10/2006 | Wang ................ C08G 77/045 528/21 |
| 2007/0148476 A1 * | 6/2007 | Khanarian et al. ........... 428/447 |
| 2009/0005518 A1 | 1/2009 | Just et al. |
| 2011/0144278 A1 | 6/2011 | Weissenbach et al. |
| 2011/0282024 A1 | 11/2011 | Weissenbach et al. |
| 2013/0253144 A1 | 9/2013 | Weissenbach et al. |

FOREIGN PATENT DOCUMENTS

| EP | 0 518 057 A1 | 12/1992 |
|---|---|---|
| EP | 1 331 238 A2 | 7/2003 |
| EP | 1 331 238 A3 | 7/2003 |
| WO | WO 2013/076032 A1 | 5/2013 |
| WO | WO 2013/076036 A1 | 5/2013 |

OTHER PUBLICATIONS

U.S. Appl. No. 14/360,120, filed May 22, 2014, Standke, et al.
International Search Report issued Mar. 21, 2013, in PCT/EP2012/072969.

\* cited by examiner

*Primary Examiner* — Marc Zimmer
(74) *Attorney, Agent, or Firm* — Oblon, McClelland, Maier & Neustadt, L.L.P.

(57) ABSTRACT

The invention relates to a composition containing olefinically functionalized siloxane oligomers which are derived from olefinically functionalized alkoxy silanes and optionally alkoxy silanes functionalized with saturated hydrocarbons and optionally a tetraalkoxysilane, at most comprising an olefinic group on the silicon atom having a reduced chloride content and the VOC content being lower with respect to the hydrolysable alkoxy-groups. The invention also relates to methods for the production thereof and to the use thereof.

35 Claims, No Drawings

MIXTURES, PARTICULARLY LOW IN VOLATILE ORGANIC COMPOUNDS (VOC), OF OLEFINICALLY FUNCTIONALISED SILOXANE OLIGOMERS BASED O ALKOXY SILANES

CROSS REFERENCE TO RELATED APPLICATIONS

The present application is a 35 U.S.C. §371 national stage patent application of International patent application PCT/EP2012/072969, filed on Nov. 19, 2012, published as WO/2013/076035 on May 30, 2013, the text of which is incorporated by reference, and claims the benefit of the filing date of German application no. 10 2011 086 863.1, filed on Nov. 22, 2011, the text of which is also incorporated by reference.

The present invention relates to selected, particularly low-VOC compositions of olefinically functionalized siloxane oligomers, derived from olefinically functionalized alkoxysilanes, which may take the form of a mixture of olefinically functionalized siloxane oligomers, and which have not more than one olefinic radical per silicon atom, and also to processes for preparing them and to their use.

It is long-established practice to use mixtures of catenary and cyclic siloxane oligomers in the production of thermoplastics and of elastomers. Increasingly now, however, efforts are made to work in as low-VOC a way as possible, for example in the crosslinking of thermoplastics and also of elastomers, particularly in the production of cables (VOC—Volatile Organic Compounds).

It is known practice to react vinyltriethoxysilane, optionally in mixtures with alkyltriethoxysilanes and/or tetraethoxysilane, by acidic HCl catalysed hydrolysis and condensation in an alcohol in the presence of a calculated amount of water. The alcohol is subsequently removed.

The acid used remains in the product or, in the case of the hydrochloride or hydrogen chloride (HCl), must be removed from the crude products again, at cost and inconvenience, after the reaction of the organofunctional alkoxysilanes, so as not to contribute to corrosion of the metallic surfaces of the processing machinery. This is done by distillation of the crude siloxane products.

In the application, such as in the production of filled cable compounds, for example, the oligomers are generally employed together with polymers and functional fillers in compounding machines. In the case of batch processes, this takes place in internal mixers or on mixing rolls, and, in the case of continuous compounding operations, it takes place in twin-screw extruders or co-kneaders. The typical processing temperatures here are in the 130-270° C. range; accordingly, at the points where the silane compound is added—depending on the process, this is the inlet of the compounding machine or the polymer melt—as an inevitable result of the process, temperatures prevail which are above the boiling temperature of the silane monomers and distillable oligomers. Experience teaches that in addition to the unwanted loss of active substance, there is also increased incidence of deposition of free silane compounds on the internal housing walls or on the devolatilizing zones. These deposits are based on products of degradation of the vaporized silanes or distillable oligomers. Critical situations may arise as a result of these possibly alcohol-containing vapours, which in the case of backwards devolatilizing may enter the intake area and may come into contact with hot surfaces. This challenge also applies in part-filled zones of the compounding assemblies, or in their devolatilizing zones. Overall, for these reasons, the compounds used must have a very high flash point. Account must also be taken of the liberated hydrolysis alcohol, which is produced, in the case of filled polymer compounds, during the hydrolysis reaction of the ester groups of the silicon-functional group of the silane or silane oligomer in the compound. Overall, therefore, reducing the VOC (volatile organic compounds) is a very important criterion with this technology.

As already mentioned, the customary operating temperatures for the compounding operation are usually above 101° C., and kneading, for example, takes place frequently at 170 to 180° C. Consequently there continues to be a requirement for reduced-VOC and low-corrosion oligomers which as far as possible no longer contain any acidic compounds, such as formic acid, HCl or Cl-containing compounds. Even miniscule amounts of these compounds lead to corrosion at the stated operating temperatures, and hence to wear of the machine components after brief downtime periods. For stainless steels, nickel-based alloys and copper-based alloys, for instance, it is said that they are not resistant, owing to the corrosion that occurs, with respect to formic acid or HCl (see, for example, Handbuch der Metallbeläge, Witzemann, January 2010, Section 7.2 Corrosion Resistance, pp. 200-238). In a brochure (Chemische Beständigkeit der Nirosta®-Stähle, ThyssenKrupp Nirosta GmbH, Edition 3, January, 2008), ThyssenKrupp describes various types of corrosion and names typical triggers for erosive surface corrosion in the form of perforation corrosion, gap corrosion or stress crack corrosion, such as the presence of acids and chloride ions. The corrosive effect of acids and chloride ions increases markedly with elevated temperature. The removal of mass from unalloyed steels at high atmospheric humidity (80 to 100% relative atmospheric humidity) in the presence of formic acid may amount to 10 g/m$^2$, and in the presence of chlorides may amount to up to 105 g/m$^2$, after 14 days. Accordingly, the amount of hydrolysis and condensation catalysts in the oligomers prepared in accordance with the invention is as far as possible to be reduced down to a level in the weight ppm to weight ppt range or down to the detection limit.

As well as the corrosion during processing, however, an important part is also played by the presence of chloride/chloride ions or acids in the end application, e.g. in cable insulation systems. As well as the possible corrosion on the insulated current conductor, and the possible negative effect on the electrical properties of the cable insulation itself, it is absolutely necessary to avoid corrosive and halogen-containing combustion gases in the case of halogen-free compounds containing flame retardants. This requirement applies, of course, to all raw materials employed in these compounds.

Through the aforesaid avoidance or minimization of the chloride fractions and acid fractions in the siloxane oligomers of the invention, it would be possible to meet these challenges in full.

Moreover, increasing interest is being focused on silane systems which contain increasingly less organic solvent and therefore are more eco-friendly. For this reason, the trend is toward providing precondensed, lower-VOC silane systems, which then, however, must be stabilized, since they still contain the catalyst, or from which the catalyst must be removed, in a costly and inconvenient procedure.

EP 0 518 057 B1 discloses a process for preparing mixtures of catenary and cyclic siloxane oligomers. According to Examples 1 and 6, the respective product mixtures are prepared by hydrolysis and condensation of vinyltrialkoxysilanes, or of a mixture of vinyl- and alkyltrialkoxysilanes, the hydrolysis and condensation being carried out using 0.63 mol of water per mole of Si in the silane employed. With the method disclosed therein, moreover, the HCl catalyst cannot be fully removed, and a corrosive residue amounting to about 50 to about 230 ppm of HCl remains even in products distilled in accordance with the process disclosed.

Mixtures of oligomeric alkoxysilanes obtained accordingly contain a high fraction of alkoxy groups, since, in accordance with the amount of water used for the hydrolysis, only a small fraction of hydrolysis alcohol is formed in the reaction, and there is still a high VOC fraction in the oligomer mixture, which may be released in the form of alcohol on ingress of water in the application of the oligomer mixture. Additionally, alcohol may be released on ingress of moisture or by continuing condensation in the oligomer mixture. If alcohol is released in this way during storage of the oligomer mixture, the result is generally an unwanted drop in the flash point. A product according to EP 0 518 057 B1 is subjected to exacting distillation even as part of the work-up procedure, under vacuum, in a costly and energy-intensive way. Said oligomer mixtures find application as crosslinking agents for thermoplastic polyolefins by graft polymerization and hydrolytic condensation.

U.S. Pat. No. 6,395,856 B1 discloses hydrosilylation of oligomers containing organofunctional silicon, such as the hydrosilylation of vinylmethoxysiliconates from the reaction of vinyltrimethoxysilane in the presence of formic acid, under inert gas, without the presence of a diluent.

CN 100343311 C describes silane oligomers obtained by catalytic hydrolysis and condensation of vinyltrimethoxysilane. The use of metal salt catalysts, such as copper hydroxide, for example, in combination with acids is mandatory. The removal of the catalysts is costly and inconvenient and it is likely that catalyst residues and/or neutralization products remain in the product and have deleterious effects in numerous applications. The aim here, accordingly, is for removal of the acid by neutralization with calcium carbonate and filtration of the calcium salt formed in this procedure.

In the prior art, for a number of siloxane oligomers, the flash point drops within a few days in the course of storage to below 50° C., owing to possibly excessive concentrations of catalyst residues in the composition. Other compositions from the prior art, in turn, exhibit excessive mass losses of up to 25 wt % at 150° C., and a large mass loss of around 50 to 90 wt % at 200° C.

Siloxanes with high molecular weights in the 10 000 g/mol range are described in JP10 298289 A, being prepared by hydrolysis and precondensation or condensation of a vinyl- or phenyl-functional alkoxysilane in the presence of an acid catalyst, the catalyst being subsequently removed from the product mixture by means of an anhydrous anionic ion exchanger. In the majority of applications, material of such high molecular weight cannot be used, owing to high viscosities and inadequate reactivity.

Organosiloxane oligomers with a multiplicity of possible functionalities, an average molecular weight Mn in the range of 350-2500 g/mol and a polydispersity (D=Mw/Mn) of 1.0-1.3 are described in JP 2004 099872. The preparation takes place in the presence of a basic catalyst from a very diluted aqueous solution with a very low, economically unproductive space-time yield; accordingly, 1 l of solution yielded 1 ml of isolated product. The teaching of JP2004 099872A could not be reproduced in the manner disclosed. For instance, a number of times, Example 1 could not be reproduced in the manner indicated.

It was an object of the present invention to provide further, particularly low-VOC mixtures of purely olefinic siloxane oligomers, based more particularly on alkenylalkoxysilanes, or particularly low-VOC mixtures of olefinically functionalized and alkyl-functionalized siloxane oligomers, based more particularly on alkenyl-/alkyl-alkoxysilanes, and also to provide a process for preparing such mixtures. An additional concern was to use the low-VOC siloxane oligomers of the invention to improve processability with thermoplastics or elastomers and also to improve the performance of the thermoplastics or elastomers produced therewith. Moreover, the siloxane oligomers ought to have very high flash points, and to be validly low-VOC even at high temperatures, and ought to be able to be used in the practical art at elevated temperatures without further safety measures. The siloxane oligomers themselves, as well, are to exhibit only small losses in mass at high temperatures, such as in extruders, for example. A key point with regard to processability is also the rapid dispersibility of the siloxane oligomers in the thermoplastics, in combination with extremely low losses of mass at the prevailing temperatures in extruder applications. Additionally it may be of advantage if the chlorine content, more particularly the total chloride content and/or else the hydrolysable chloride content, is as small as possible. Furthermore, the olefinic siloxane oligomers ought to exhibit high storage stability even over prolonged storage periods and at the same time, preferably, an increase in the viscosity as well, as a result, for example, of gelling or of flocculation or of ongoing condensation of the mixture, is to be avoided over a relatively long period of time.

Furthermore, the amount of monomers in the olefinically functionalized siloxane oligomers ought to be low, or preferably there ought to be no longer any monomers present that can lead to unwanted post-crosslinking, and at the same time the process ought to be more economically productive than its known counterparts. A further aim at the same time was to bring about a degree of oligomerization for the siloxanes, with low VOC content and a viscosity of ≤3000, more particularly of less than or equal to 1000 mPa s and preferably greater than or equal to 5 mPa s, in order to ensure the best possible processing qualities of the siloxane oligomers in the application.

The objects are achieved in accordance with the independent claims; preferred embodiments are set out in the dependent claims and in the description in detail.

Surprisingly it has been found that olefinically functionalized alkoxysilanes and optionally alkylalkoxysilane and optionally tetraalkoxysilane can be readily and economically converted by reaction with a defined amount of water of greater than or equal to 1.1 to 1.59 mol of water per mole of silicon atoms in the alkoxysilanes used—1.0 to 1.6 or 1.60 mol of water may also be judicious—and optionally in the presence of a solvent, preferably alcohol, into compositions of particularly low-VOC olefinic siloxane oligomers, with the hydrolysis alcohol and the solvent optionally present being substantially removed; in particular, only the solvent and/or the hydrolysis alcohol are/is removed by distillation. The fact that the siloxane oligomers obtained in this way, already in the form of the liquid-phase product, exhibit a very low total chloride content was a surprise. The compositions obtained accordingly have a particularly low chloride content and a particularly low VOC content in accordance with the invention.

In contrast to the known oligomers, the compositions of the invention and the siloxane oligomer compositions prepared by the process of the invention require no further working-up, such as distillation of the compositions of the siloxane oligomers, for example. The composition prepared, the liquid-phase siloxane oligomer product, exhibits equal or improved performance relative to known siloxane oligomers which, however, have been purified by distillation, and are obtained according to a somewhat different process. In accordance with the invention, therefore, the resulting siloxane oligomer need no longer be itself distilled, but can instead be obtained and used purely as the liquid-phase product. The composition may therefore also be obtained with a greater yield.

The invention accordingly provides a composition comprising olefinically functionalized siloxane oligomers having not more than one olefinic radical on the silicon atom, and the olefinically functionalized siloxane oligomers have Si—O-crosslinked structural elements which form catenary, cyclic, crosslinked and/or three-dimensionally crosslinked structures, with at least one structure corresponding in idealized form to the general formula I,

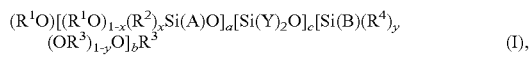

(I), wherein the structural elements are derived from alkoxysilanes and

A in the structural element corresponds to an olefinic radical and is selected in particular from a linear, branched or cyclic alkenyl- or cycloalkenyl-alkylene-functional group having in each case 2 to 16 C atoms, B in the structural element corresponds to a saturated hydrocarbon radical and is selected in particular from a linear, branched or cyclic alkyl radical having 1 to 16 C atoms, Y corresponds to $OR^3$ or, in crosslinked and optionally three-dimensionally crosslinked structures, independently of one another, to $OR^3$ or $O_{1/2}$, where $R^1$ independently at each occurrence corresponds to a linear, branched and/or cyclic alkyl radical having 1 to 4 C atoms, and/or optionally H, $R^3$ independently at each occurrence corresponds to a linear, branched and/or cyclic alkyl radical having 1 to 4 C atoms, and/or optionally to H, and $R^2$ corresponds independently at each occurrence to a linear, branched or cyclic alkyl radical having 1 to 15 C atoms, more particularly having 1 to 8 C atoms, alternatively having 1 to 6 C atoms, and $R^4$ corresponds independently at each occurrence to a linear, branched or cyclic alkyl radical having 1 to 15 C atoms, more particularly having 1 to 8 C atoms, alternatively having 1 to 6 C atoms, a, b, c, x and y independently correspond to integers with $1 \le a$, $0 \le b$, $0 \le c$, x independently at each occurrence is 0 or 1, y independently at each occurrence is 0 or 1, and $(a+b+c) \ge 2$, in particular the chlorine content, preferably total chloride content, being less than or equal to 250 mg/kg, more particularly less than or equal to 150 mg/kg, preferably less than or equal to 100 mg/kg, more preferably less than or equal to 75 mg/kg, more preferably still less than or equal to 50 mg/kg, with further preference less than or equal to 35 mg/kg, in particular in the composition in the form of a liquid-phase product, in particular, and the structural elements $[(R^1O)_{1-x}(R^2)_xSi(A)O]_a$, $[Si(B)(R^4)_y(OR^3)_{1-y}O]_b$ and $[Si(Y)_2O]_c$ overall, i.e. in total, being present preferably in the general formula I together, in relation to all silicon atoms of the general formula I, at greater than or equal to 10% as T structure, with the proviso that $1 \le a$, $0 \le b$, $0 \le c$ and $(a+b+c) \ge 2$, or alternatively that in total the structural elements $[(R^1O)_{1-x}(R^2)_xSi(A)O]_a$ are present, in relation to the total sum of silicon atoms in the general formula I, at greater than or equal to 5% as T structure, more particularly at greater than or equal to 7.5%, preferably at greater than or equal to 10%, more preferably at greater than or equal to 11%, more preferably still at greater than or equal to 13%, with further preference at greater than or equal to 15%, alternatively at greater than or equal to 20% or, according to a further alternative, at greater than or equal to 25%. Also disclosed is that the structural elements $[(R^1O)_{1-x}(R^2)_xSi(A)O]_a$, $[Si(B)(R^4)_y(OR^3)_{1-y}O]_b$ and $[Si(Y)_2O]_c$ overall, i.e. in total, in the general formula I are present together, in relation to all silicon atoms of the general formula I, at greater than or equal to 5%, preferably at greater than or equal to 10%.

The invention likewise provides a composition comprising olefinically functionalized siloxane oligomers which have not more than one olefinic radical on the silicon atom, and the olefinically functionalized siloxane oligomers have Si—O-crosslinked structural elements which form catenary, cyclic, crosslinked and/or three-dimensionally crosslinked structures, with at least one structure corresponding in idealized form to the general formula I, the siloxane oligomers having derived structural elements from at least one of the alkoxysilanes, (i) from olefinically functionalized alkoxysilanes of the general formula II,

(II)

where A corresponds to an olefinic radical and is selected more particularly from a linear, branched or cyclic alkenyl- or cycloalkenyl-alkylene-functional group having in each case 2 to 16 C atoms, where $R^2$ independently at each occurrence is a linear, branched or cyclic alkyl radical having 1 to 15 C atoms, and x independently at each occurrence is 0 or 1, x preferably being 0, and $R^1$ independently corresponds to a linear, branched and/or cyclic alkyl radical having 1 to 4 C atoms, more particularly to a methyl, ethyl or propyl group, or optionally from a mixture of alkoxysilanes of the formula II or transesterification products, and (ii) optionally from alkoxysilane of the formula III functionalized with a saturated hydrocarbon radical,

(III)

where B corresponds to an unsubstituted hydrocarbon radical and more particularly is selected from a linear, branched or cyclic alkyl radical having 1 to 16 C atoms, where $R^4$ independently at each occurrence is a linear, branched or cyclic alkyl radical having 1 to 15 C atoms, and y independently at each occurrence is 0 or 1, and $R^3$ independently corresponds to a linear, branched and/or cyclic alkyl radical having 1 to 4 C atoms, more particularly to a methyl, ethyl or propyl group, with B preferably being a methyl, ethyl or propyl, and y preferably being 0, or optionally a mixture of alkoxysilanes of the formula III or the transesterification products thereof, and (iii) optionally from a tetraalkoxysilane of the general formula IV $Si(OR^3)_4$ where $R^3$ independently at each occurrence is as defined above, with a chlorine content, more particularly total chloride content, of less than or equal to 250 mg/kg, the structural elements being present together, in relation to all silicon atoms of the siloxane oligomer, at greater than or equal to 10% as T structure.

It is likewise disclosed that the structural elements together, in relation to all silicon atoms of the siloxane oligomer, are present at greater than or equal to 5% as T structure, more particularly at greater than or equal to 7.5%, preferably at greater than or equal to 10%, more preferably at greater than or equal to 11%, more preferably still at greater than or equal to 13%, with further preference at greater than or equal to 15%, alternatively at greater than or equal to 20% or, according to one further alternative, at greater than or equal to 25%.

The chlorine content, preferably total chloride content, is preferably less than or equal to 250 mg/kg, more preferably less than or equal to 35 mg/kg down to the detection limit. Down to preferably less than or equal to 0.001 mg/kg.

The invention provides compositions in which less than or equal to 15% (area %, GPC) of disiloxanes and tricyclosiloxanes are present, more preferably less than or equal to 12%, with, in particular, greater than or equal to 10% of T structures occurring in the siloxane oligomers, with the amount of trisiloxanes, cyclotetrasiloxanes, tetrasiloxanes, cyclopentasiloxanes, pentasiloxanes and/or cyclohexasiloxanes being preferably greater than or equal to 60 area % (GPC), more preferably greater than or equal to 65%, very preferably greater than or equal to 70% (area %, GPC) in the overall composition. Alternatively or additionally with preference the amount of trisiloxanes, cyclotetrasiloxanes, tetrasiloxanes and cyclopentasiloxanes is already greater than or equal to 40 area % (GPC), preferably greater than or equal to 45%, more preferably greater than or equal to 50%, more preferably greater than or equal to 55%, very preferably greater than or equal to 60%, and especially less than or equal to 65% (area %, GPC) in the overall composition. It is generally the case that the designation disiloxane, trisiloxane, tetrasiloxane, pentasiloxane covers the siloxanes that are linear and/or branched in each case, and cyclotrisiloxane, cyclotetrasiloxane, cyclopenta- or cycloheptasiloxane covers the cyclic siloxanes.

The amount of trisiloxanes and cyclotetrasiloxanes may also already be greater than or equal to 15 area % (GPC), preferably greater than or equal to 20% (area %, GPC) in the overall composition. And preferably less than or equal to 50%, more preferably less than or equal to 20%, very preferably less than 15%. Alternatively or additionally with preference the amount of tetrasiloxanes and cyclopentasiloxanes is already greater than or equal to 20 area % (GPC), preferably greater than or equal to 25%, more preferably greater than or equal to 30% (area %, GPC) in the overall composition, and preferably less than or equal to 50%, more preferably less than or equal to 40%. With particular preference greater than or equal to 70% of the siloxane oligomers are present in the composition in the form of disiloxane, cyclotrisiloxane, trisiloxane, cyclotetrasiloxane, tetrasiloxane, cyclopentasiloxane, pentasiloxane and/or cyclohexasiloxane, preferably greater than or equal to 75%, more preferably greater than or equal to 80%, more preferably still greater than or equal to 85%, preferably greater than or equal to 90%. In the TGA, these particularly preferred siloxane oligomer compositions exhibit a mass loss of greater than or equal to 50% only at above 240° C., more preferably above 250° C., and the temperature at which the mass loss of 50% occurs may also be up to 530° C.

Likewise provided by the invention are compositions in which greater than or equal to 30% (area %, GPC) have an Mw of 500 to 750 (rel. Mw), more particularly greater than or equal to 30% to 50% have an Mw of 500 to 750, more preferably 35% to 45%.

The compositions of the invention comprising siloxane oligomers exhibit preferably at 150° C. (TGA) only a mass loss of less than 5%, and more preferably at 200° C. only a mass loss of less than or equal to 20%, more particularly less than or equal to 15%, more preferably less than or equal to 10% (mass loss in wt %).

The compositions obtainable in accordance with the invention are therefore outstandingly suitable for use in hot extruders, since even at very high temperatures they release little VOC, exhibit a constantly very low mass loss and exhibit properties that are homogenous in the application by virtue of a constantly low mass distribution. As a result of the particularly adjusted molar mass distribution, more particularly in the area of the trisiloxanes, cyclotetrasiloxanes, tetrasiloxanes, cyclopentasiloxanes, pentasiloxanes and/or cyclohexasiloxanes, homogeneous and rapid dispersion is enabled in the polymers and prepolymers, such as PE, PP, etc., and at the same time the mass loss during processing can be kept very small.

In addition, preferred compositions comprising olefinically functionalized siloxane oligomers and also, in particular, siloxane oligomers of the formula I have a weight-average molecular weight (Mw) of greater than or equal to 500 g/mol, more particularly greater than or equal to 520 to 1100 g/mol, preferably 520 to 800 g/mol, more preferably 550 to 770 g/mol, and the number-average molecular weight (Mn) is preferably greater than or equal to 450 g/mol, more particularly up to 800 g/mol, preferably greater than or equal to 450 to 650 g/mol, and the polydispersity is preferably 1.1 to 1.8, preferably 1.13 to 1.45, more preferably 1.1 to 1.3, more preferably still 1.1 to 1.25 or 1.1 to 1.21.

Particularly preferred are compositions comprising olefinically functionalized siloxane oligomers and also, in particular, siloxane oligomers of the formula I having a weight-average molecular weight (Mw) of greater than or equal to 564 to 1083 g/mol. At the same time, preferably, greater than or equal to 85%, preferably 90% (area %, GPC) have a molecular weight (Mw) of less than 1000 g/mol. In particular in combination with an Mw of greater than or equal to 30% (area %, GPC, Mw) of 500 to 750 (rel. Mw), greater than or equal to 30% to 50% preferably have an Mw of 500 to 750, more preferably 35% to 45%. All figures should always be understood as being in relation to the overall composition.

Particularly preferred compositions have olefinically functionalized siloxane oligomers which are present at greater than or equal to 30% (area %, GPC), more particularly greater than or equal to 30% to less than or equal to 50%, more preferably 35% to 50% in relation to the overall composition with a molecular weight (Mw) of 500 to 700 g/mol in the composition. Likewise preferred compositions comprise olefinically functionalized siloxane oligomers which are present at greater than or equal to 60% (area %, GPC) as trisiloxane, tetrasiloxane, pentasiloxane, cyclotetrasiloxane, cyclopentasiloxane and/or cyclohexasiloxane and also as a mixture comprising at least two of the aforementioned siloxanes, more particularly to an extent of greater than or equal to 65%, preferably greater than or equal to 70%. It is particularly preferred here if in particular at the same time the mass loss of a composition of the invention of 50 wt %, determined by TGA, occurs at a temperature above 240° C., more particularly above 250° C. Furthermore, the compositions, with particular preference for the stated applications in extruders, exhibit a loss of mass by the composition as determined by TGA (platinum crucible, lid with hole, 10 K/min) at a temperature up to and including 150° C. under of less than or equal to 5 wt %, more particularly less than or equal to 1 to 4 wt %, preferably less than or equal to 1 to 3 wt %. Furthermore, alternatively or additionally, the compositions exhibit a loss of mass by the composition as determined by TGA (platinum crucible, lid with hole, 10 K/min) at a temperature up to and including 200° C. of less than 20 wt %, more particularly less than or equal to 15 wt %, preferably less than or equal to 10 wt %, alternatively between 3 to 15 wt %.

Weight-average molecular weight (Mw)

$$M_w = \frac{\sum n_i M_i^2}{\sum n_i M_i}$$

and number-average molecular weight (Mn)

$$M_n = \frac{\sum n_i M_i}{\sum n_i}$$

in each case with $n_1$=amount of substance [mass] of the i-mer, $M_1$=molar mass of the i-mer. Details relating to the definition for weight average and number average, which are known per se to the skilled person, may alternatively be found by the reader from sources including the Internet, at http://de.wikipedia.org/wiki/Molmassenverteilung, or from a standard work of mathematics.

In the process of the invention, alkoxysilanes of the formula II with x being 0 can be reacted on their own, or else with alkoxysilanes of the formula III in which y is 1 or 0.

All alkyl radicals, such as $R^1$, $R^2$, $R^3$ and $R^4$, with 1 to 4 C atoms may in each case independently of one another be preferably methyl, ethyl, propyl, n-propyl, isopropyl, butyl, n-butyl, isobutyl, tert-butyl and/or, with 5 C atoms, 2-methylbutyl. The alkyl radicals $R^2$ and $R^4$ here may correspond independently at each occurrence to a linear, branched or cyclic alkyl radical having 1 to 15 C atoms. The alkyl radicals $R^2$ and $R^4$ may independently at each occurrence be selected from a methyl, ethyl, propyl, butyl, isobutyl, n-butyl, tert-butyl, pentyl, n-pentyl, isopentyl, neopentyl, hexyl, isohexyl, neohexyl, cyclohexyl, 2,2-dimethylbutyl, 2,3-dimethylbutyl, 2-methylpentyl, 3-methylpentyl, octyl, n-octyl, isooctyl, nonyl, decyl, undecyl, dodecyl, $C_{13}H_{27}$, $C_{14}H_{29}$ and a $C_{15}H_{31}$ group or cyclopentyl, cyclohexyl, and also an alkyl-substituted cyclopentyl and cyclohexyl group.

Transesterification products may comprise alkoxysilanes having different alkoxy groups, such as, for example, alkoxysilanes functionalized with methoxy and ethoxy groups and of the formulae II, II, IV or else of the formula I. The siloxane oligomers and the alkoxysilanes of the formulae II, III and IV may be present in the form of transesterification products. Thus, for example, the alkoxysilanes of the formula II may be present in the form of mixtures of methoxysilanes, ethoxysilanes, or methoxyethoxysilanes with mixed functionalization. Correspondingly, the alkoxysilanes of the formula III may also be mixtures of methoxysilanes, ethoxysilanes, or methoxyethoxysilanes with mixed functionalization. Corresponding comments apply to the olefinically functionalized siloxane oligomers, more particularly of the formula I; as $R^1$ and $R^3$ they may have methyl or ethyl groups and also both groups, and may be present in the form of methoxy- and ethoxy-functionalized oligomers.

In addition to the aforementioned features, the amount of monomers alkoxysilanes in the composition of the invention is significantly reduced. The invention therefore also provides a composition comprising olefinically functionalized siloxane oligomers in which the amount of silicon atoms of monomeric alkoxysilanes is less than or equal to 3% down to the detection limit or 0.0% in relation to all silicon atoms, preferably less than 2% to 0.0%, more preferably less than or equal to 1.5% to 0.0%, and alternatively preferably less than or equal to 2% to 0.0 wt %, more preferably less than or equal to 1 wt %, the amount of monomers being more preferably still less than or equal to 0.5 to 0.0 wt %, with further preference less than 0.3 to 0.0 wt %. Considered to be monomeric alkoxysilanes are the alkoxysilanes of the formulae II, III and/or IV and also their monomeric hydrolysis products. The amount in per cent can be determined by means, for example, of $^{29}Si$ NMR spectroscopy.

According to particularly preferred embodiments, the olefinic radical A in formulae I and/or II corresponds to a non-hydrolysable olefinic radical, more particularly to a linear, branched or cyclic, alkenyl- or cycloalkenyl-alkylene-functional group having in each case 2 to 16 C atoms, preferably to a vinyl, allyl, butenyl, such 3-butenyl, pentenyl, hexenyl, ethylhexenyl, heptenyl, octenyl, cyclohexenyl-C1 to C8-alkylene, preferably cyclohexenyl-2-ethylene, such as 3'-cyclohexenyl-2-ethylene and/or cyclohexadienyl-C1 to C8-alkylene, preferably cyclohexadienyl-2-ethylene group.

Also preferably the unsubstituted hydrocarbon radical B independently in formulae I and/or III may correspond to a linear, branched or cyclic alkyl radical having 1 to 16 C atoms, more particularly a methyl, ethyl, propyl, n-propyl, isopropyl, butyl, n-butyl, isobutyl, n-octyl, isooctyl, octyl, or hexadecyl group. Also preferably the radical B may independently be selected from tert-butyl, pentyl, n-pentyl, isopentyl, neopentyl, hexyl, isohexyl, neohexyl, heptyl, 2,2-dimethylbutyl, 2,3-dimethylbutyl, 2-methylpentyl, 3-methylpentyl, neooctyl, nonyl, decyl, undecyl, dodecyl, 2-methylheptyl, 3-methylheptyl, 4-methylheptyl, 2,2-dimethylhexyl, 2,3-dimethylhexyl, 2,4-dimethylhexyl, 2,5-dimethylhexyl, 3,3-dimethylhexyl, 3,4-dimethylhexyl, 3-ethylhexyl, 2,2,3-trimethylpentyl, 2,2,4-trimethylpentyl, 2,3,3-trimethylpentyl, 2,3,4-trimethylpentyl, 3-ethyl-2-methylpentyl, 3-ethyl-3-methylpentyl, 2,2,3,3-tetramethylbutyl, $C_{13}H_{27}$, $C_{14}H_{29}$ and a $C_{15}H_{31}$ group. According to one alternative, the alkyl radical may be branched or cyclic with 3 to 16 C atoms, or linear with 2 to 7 C atoms.

It is particularly preferred if in formulae I and/or II, the olefinic radical A is a vinyl group, and independently thereof, in formulae I and/or III, the unsubstituted hydrocarbon radical B is selected from a methyl, ethyl, propyl, butyl, isobutyl, n-butyl, tert-butyl, pentyl, n-pentyl, isopentyl, neopentyl, hexyl, isohexyl, neohexyl, 2,2-dimethylbutyl, 2,3-dimethylbutyl, 2-methylpentyl, 3-methylpentyl, heptyl, octyl, n-octyl, isooctyl, nonyl, decyl, undecyl, dodecyl, $C_{13}H_{27}$, $C_{14}H_{29}$, $C_{15}H_{31}$ and hexadecyl group, and independently at each occurrence $R^1$ is a methyl, ethyl or propyl group and $R^3$ independently is a methyl, ethyl or propyl group.

In accordance with the invention the structural elements $[(R^1O)_{1-x}(R^2)_xSi(A)O]_a$, $[Si(B)(R^4)_y(OR^3)_{1-y}O]_b$ and $[Si(Y)_2O]_c$ in the general formula I together are present, in relation to all silicon atoms of the general formula I at greater than or equal to 10% as T structure, more particularly at greater than or equal to 11%, preferably at greater than or equal to 13, more preferably at greater than or equal to 15%, alternatively at greater than or equal to 20% or, according to a further alternative, at greater than or equal to 25%. Judiciously it is also possible for greater than or equal to 7.5% to be present as T structure.

The olefinically functionalized siloxane oligomers likewise preferably have a ratio of silicon atoms to A and B radicals, with the proviso that a is greater than or equal to 1, b is greater than or equal to 0 and c is greater than or equal to 0, and (a+b+c) is greater than or equal to 2, of Si to (A+B radicals) of 1:1 to about 1.22:1, preferably of 1:1 to 1.15:1.

Likewise provided by the invention are compositions comprising olefinically functionalized siloxane oligomers, and also processes for preparing the compositions, which have not more than one olefinic radical on the silicon atom and in which in particular, selected in each case independently of one another, (i) the structural element $[(R^1O)_{1-x}(R^2)_xSi(A)O]_a$ in the general formula I is present, in relation to all silicon atoms of the general formula I, at greater than or equal to 5%, more particularly at greater than or equal to 7.5%, as T structure, with further preference at greater than or equal to 10%, preferably at greater than or equal to 11%, more preferably at greater than or equal to 15%, alternatively at greater than or equal to 20% or, according to another alternative, at greater than or equal to 25%, and optionally (ii) the structural elements $[(R^1O)_{1-x}(R^2)_xSi(A)O]_a$ and $[Si(B)(R^4)_y(OR^3)_{1-y}O]_b$ and $[Si(Y)_2O]_c$ in the general formula I are present together, in relation to all silicon atoms of the general formula I, at greater than or equal to 50% as D structure, more particularly at greater than or equal to 55%, preferably at greater than or equal to 57.5%, more preferably at greater than or equal to 60%, and optionally (iii) the structural element $[(R^1O)_{1-x}(R^2)_xSi(A)O]_a$ is present in the general formula I, in relation to all silicon atoms of the general formula I, at less than or equal to 35% as M structure, more particularly at less than or equal to 30%, preferably at less than or equal to 25%, more preferably at less than or equal to 20%, alternatively at less than or equal to 20% or, according to a further alternative, at less than or equal to 15%, and preferably at greater than 3%, and optionally (iv.a) the structural element $[Si(B)(R^4)_y(OR^3)_{1-y}O]_b$ in the general formula I is present, in relation to all silicon atoms of the general formula I, at less than or equal to 35% as M structure, more particularly less than or equal to 30%, preferably less than or equal to 25% as M structure, more particularly at less than or equal to 22%, preferably at less than or equal to 20%, more preferably at less than or equal to 18%, alternatively preferably at less than or equal to 15%, and preferably greater than 7%, and/or optionally (iv.b) the structural element $[Si(B)(R^4)_y(OR^3)_{1-y}O]_b$ in the general formula I is present at greater than or equal to 5% as T structure, more particularly at greater than or equal to 7.5%, more particularly at greater than or equal to 10%, preferably at greater than or equal to 11%, more preferably at greater than or equal to 15%, alternatively at greater than or equal to 20% or, according to another alternative, at greater than or equal to 25%, and/or optionally (v) the structural element $[Si(Y)_2O]_c$ in the general formula I is present at greater than or equal to 20% as D structure, or, more particularly, more than 40% of the structural elements $[Si(Y)_2O]_c$ in the general formula I are present as D structure, more particularly more than 45%, preferably more than 50%, more preferably more than 55%.

Likewise provided by the invention are compositions comprising olefinically functionalized siloxane oligomers, and also processes for preparing the compositions, which have not more than one olefinic radical on the silicon atom and in which, selected independently of one another in each case, (iii) the structural element $[(R^1O)_{1-x}(R^2)_x(Si(A)O]_a$ is present in the general formula I, in relation to all silicon atoms of the general formula I, at less than or equal to 35% as M structure, more particularly at less than or equal to 30%, preferably at less than or equal to 25%, more preferably at less than or equal to 20%, alternatively at less than or equal to 20% or, according to another alternative, at less than or equal to 15%, and preferably greater than 3%, and, if present, (iv.a) the structural element $[Si(B)(R^4)_y(OR^3)_{1-y}O]_b$ in the general formula I is present, in relation to all silicon atoms of the general formula I, at less than or equal to 20%, more particularly at less than or equal to 18%, preferably at less than or equal to 15%, and preferably greater than 7%.

According to one alternative, the invention provides compositions comprising olefinically functionalized siloxane oligomers which have not more than one olefinic radical on the silicon atom, more particularly of the general formula I, with the proviso that a is greater than or equal to 1 and b and c are 0, i.e. purely olefinic siloxane oligomers without alkyl groups.

Likewise provided by the invention are compositions comprising olefinically functionalized siloxane oligomers which have not more than one olefinic radical on the silicon atom, more particularly of the general formula I, with the proviso that a and b are greater than or equal to 1 and c is 0, more particularly without Q structures, i.e. purely olefinically and alkyl-functionalized siloxane oligomers without $Si(O—)_4$ groups and without $Si(O—)_4$ fragments which form Q structures. The two abovementioned compositions on the basis of these conditions the desired viscosity on and in their application exhibit outstanding properties in terms of their processing, application to surfaces or incorporation into polymer.

According to a further alternative, specifically preferred compositions comprising olefinically functionalized siloxane oligomers which have not more than one olefinic radical on the silicon atom and in which the structural element $[(R^1O)_{1-x}(R^2)_xSi(A)O]_a$ in the general formula I, in relation to all the silicon atoms of the general formula I, with a being greater than or equal to 1, b being greater than or equal to 0 and c being greater than or equal to 0, have from 3% and 35% of M structures, more particularly 5% to 33% of M structures, more preferably from 5% to 25%, more particularly with the proviso that the structural element $[(R^1O)_{1-x}(R^2)_xSi(A)O]_a$ in the general formula I are present at the same time at from 50% and 75% as D structure, preferably from 50% and 70%, and optionally, in addition, greater than or equal to 8% are present as T structure, more particularly greater than or equal to 10%. In the alternative with, additionally, b greater than or equal to 1, the structural element $Si(B)(R^4)_y(OR^3)_{1-y}O]_b$ in the general formula I is present at from 3% and 35% as M structure, more particularly with the proviso that c is 0. According to the alternative with a, b and c greater than or equal to 1, the siloxane oligomers, in the total of all silicon atoms, have less than 8% of T structures; in particular, the main structure of the structural element $[(R^1O)_{1-x}(R^2)_xSi(A)O]_a$ in the general formula I has less than 5% of T structures. These compositions as well still show the desired viscosity, in particular with less than 5% of T structures, and additionally the saturated hydrocarbon radical B has preferably 1 to 6 C atoms, more preferably 1 to 4 C atoms.

The amount of M, D, T or Q structures present is determined according to a method known to the skilled person, such as preferably by means of $^{29}Si$ NMR.

The ratio of M:D:T structures in the olefinic siloxane oligomers of the invention is preferably 5:10:1 to 3:5:1.

More preferably the ratio of T to D structures in all structural elements of the general formula I is in the range from 1:10 to 1:2, more particularly 1:8 to 1:3, preferably from 1:6 to 1:3, more preferably from 1:5 to 1:3, more particularly additionally to the amount of T structures of all structural elements in the general formula I of greater than or equal to 5%, preferably greater than or equal to 7.5%. Alternatively preferably the ratio of T to D structures in the olefinic siloxane oligomers is in the range from 1:10 to 1:2, more particularly 1:8 to 1:3, preferably from 1:6 to 1:3, more preferably from 1:5 to 1:3, more particularly additionally to the amount of T structures in the siloxane oligomers of greater than or equal to 5%, preferably greater than or equal to 7.5%.

Likewise preferably the ratio of M to D structures, more particularly in addition to the amount of T structures in all structural elements in the general formula I of greater than or equal to 10% of the general formula I, is in the range from 1:100 to 2.5:1, preferably 1:10 to 2.5:1, with particular preference 1:100 to 1:2, more particularly from 1:5 to 1:2, with further preference from 1:5 to 1:1, more preferably from 1:4 to 1:2, or, in one alternative, in the olefinic siloxane oligomers. Also already judicious is an amount of T structures of greater than or equal to 7.5%.

Compositions which exhibit the aforementioned structures possess a high flash point and display particularly low VOC levels in the context of the subsequent application. One noteworthy advantage of the compositions of the invention and of the process of the invention is that the olefinic siloxane oligomers prepared, more particularly the vinyl oligomers, differ from the known oligomers in requiring no further working-up, such as distillation of the compositions of the siloxane oligomers.

In accordance with the invention, catalysts employed as hydrolysis and/or condensation catalyst are acidic catalysts which are gaseous under standard conditions, more particularly HCl, and which may be dissolved in aqueous phase or alcoholic phase. A reaction therefore takes place under the conditions of homogeneous catalysis. A surprising advantage was that through the process of the invention the gaseous catalyst is successfully removed almost completely from the compositions.

A particular advantage of the olefinically functionalized siloxane oligomers of the invention is also that the reduced hydrolysable VOC content and the increased T structure content of the siloxane oligomers directly improves the processing qualities of the siloxane oligomers with polymers, as during kneading or compounding, for example. Specifically there is improvement in the melt index, thereby reducing the energy consumption in processing. Furthermore, the corrosion of the iron-containing machines goes down, since it has been possible to achieve a further reduction in the chloride content. Moreover, the water uptake capacity of the polymers compounded with the siloxane oligomers of the invention is reduced, and also, frequently, their elongation at break and also usually the tensile strength are improved. The reduced water uptake capacity is advantageous in the subsequent application sectors, such as in the production of filled cable compounds, for example, especially for cables which are to be laid in the earth and are subject to persistent moisture.

The definition of M, D, T and Q structures refers generally to the number of oxygens bonded in siloxane compounds, as illustrated below for alkoxysilyl units by way of example: with R independently at each occurrence being $OR^1$, $OR^3$, group A or group B, as defined above. With $M=[-O_{1/2}-Si(R)_3]$, $D=[-O_{1/2}-Si(R)_2-O_{1/2}-]$, $T=[RSi(-O_{1/2}-)_3]$ and $Q=[Si(-O_{1/2}-)_4]$. $-O_{1/2}-$ is always an oxygen in a siloxane bond. Accordingly, in order to be able to describe silicones and siloxanes and/or silane oligomers more illustratively, it is also possible to use the M, D, T (crosslinked) and Q (three-dimensionally crosslinked) structures rather than an idealized description by formula. For the more precise nomenclature of the designation of such siloxane structures, reference may be made to "Römpp Chemielexikon"—entry heading: Silicones. For example, from structural units M, only dimers with $M_2$, such as hexaalkoxydisiloxane, can be formed. The construction of chains requires compositions of structural units D and M, and so trimers ($M_2D$, octaalkoxytrisiloxane), tetramers ($M_2D_2$) and so on up to linear oligomers with $M_2D_n$ can be constructed. The formation of cyclic oligomers requires structural units D. In this way, for example, rings with $D_3$, $D_4$, $D_5$ or higher can be constructed. Branched and/or crosslinked structural elements, under which Spiro compounds should also be reckoned, are obtained when structural units T and/or Q are present together. Conceivable crosslinked structures may be present in the form of $T_n(n≥4)$, $D_nT_m$ (m<n), $D_nT_m$, (n>>m), $D_3T_2$, $M_4Q$, $D_4Q$ and so on, to give just a few conceivable possibilities. Structural units M are also referred to as stoppers or transfer agents, while D units are termed chain formers or ring formers, and the T, and possibly also Q, units are referred to as network formers. Thus the use of tetraalkoxysilanes, because of the four hydrolysable groups, and ingress of water and/or moisture can bring about structural units Q and hence the formation of a network (three-dimensionally crosslinked). In contrast, fully hydrolysed trialkoxysilanes may result in branches, i.e. T units $[-Si(-O-)_{3/2}]$, in a structural element, for example $MD_3TM_2$ for an oligomer having a degree of oligomerization of n=7, and in these structural representations the respective functionalities on the free valencies of the silyloxy units are to be defined.

Further details on the nomenclature comprehension of M, D, T and Q structures, and also relevant methods of analysis, include the following:

- "Strukturuntersuchungen von oligomeren und polymeren Siloxanen durch hochauflösende $^{29}$Si-Kernresonanz" [Structural analyses of oligomeric and polymeric siloxanes by high-resolution $^{29}$Si nuclear magnetic resonance], H. G. Horn, H. Ch. Marsmann, Die Makromolekulare Chemie 162 (1972), 255-267;
- "Über die $^1$H-, $^{13}$C- und $^{29}$Si-NMR chemischen Verschiebungen einiger linearer, verzweigter und cyclischer Methyl-Siloxan-Verbindungen" [On the $^1$H, $^{13}$C and $^{29}$Si NMR chemical shifts of some linear, branched and cyclic methyl-siloxane compounds], G. Engelhardt, H. Jancke; J. Organometal. Chem. 28 (1971), 293-300;
- "Chapter 8—NMR spectroscopy of organosilicon compounds", Elizabeth A. Williams, The Chemistry of Organic Silicon Compounds, 1989 John Wiley & Sons Ltd., 511-533.

It may be preferable for the composition and/or the siloxane oligomer also to have trialkylsilane groups, such as trimethylsilane or triethylsilane groups, as a result, for example, of the addition of alkoxytrialkylsilane, in order to adjust the degree of oligomerization.

To fulfil the specified objectives, preference is given to providing compositions of mixtures of olefinic siloxane oligomers wherein, in particular, more than 20 wt % of the siloxane oligomers have a degree of oligomerization of greater than or equal to 4, optionally greater than or equal to 8, i.e. the number of silicon atoms (n) per oligomer is optionally greater than or equal to 8 (n>8), and more preferably at the same time the fraction of siloxane oligomers with T structure is greater than or equal to ($≥$) 5%, more particularly greater than or equal to 6%, and at the same time the dynamic viscosity is preferably less than or equal to ($≤$) 3000 mPa s and more particularly greater than or equal to 5 mPa s, preferably less than or equal to 1000, preferably less than or equal to 500 mPa s and more particularly greater than or equal to 10 mPa s, more preferably less than or equal to 250 mPa s. It is preferred, further, if the viscosity of the composition comprising olefinically functionalized siloxanes is less than or equal to 3000 mPa s and greater than 7 mPa s, preferably less than or equal to 2500 and greater than 10 mPa s, alternatively preferably less than or equal to 1000 mPa s and greater than or equal to 12 mPa s.

Generally speaking, the siloxane oligomers may be linear and/or cyclic oligomers with M and D structures and T structure. Only on addition of tetraalkoxysilane during the preparation or before the processing of the oligomers are siloxane oligomers with M, D, Q and optionally T structures formed. Compositions of the invention have siloxane oligomers, more particularly of the formula I, in which the sum of
(a+b) is an integer greater than or equal to 2, more particularly from greater than or equal to 4 to 30, with further preference from greater than or equal to 6 to 30, with particular preference from greater than or equal to 8 to 30, and c is optionally greater than or equal to 1, such as 1 to 20, for example, more particularly 2 to 15. In the case of degrees of oligomerization that are too high, it is not possible to achieve homogeneous and reproducible product properties in the siloxane oligomers. In order to adjust the degree of oligomerization during preparation of the composition, therefore, it may be advantageous, for chain termination at a desired point in time, to add an alkoxytrialkylsilane, such as, preferably, an ethoxytrimethylsilane or methoxytrimethylsilane, to the composition that is to be prepared.

Compositions of the invention may comprise at least 20 wt % of siloxane oligomers for which the degree of oligomerization n in terms of olefinically functionalized siloxane oligomers is greater than or equal to 4, more particularly greater than or equal to 6, very preferably greater than or equal to 4, optionally greater than or equal to 8. It is further preferred here if for at least 20 wt % of the siloxane oligomers, more particularly of the formula I, the sum of (a+b) is an integer greater than or equal to 5, more particularly the sum of (a+b) is greater than or equal to 6, preferably the sum of (a+b) is greater than or equal to 4, optionally greater than or equal to 8, with a greater than or equal to 1 and b equal to 0 or b greater than or equal to 1, preferably each of a and b independently of one another greater than or equal to 2, more particularly independently greater than or equal to 4, and optionally with c in (a+b+c) greater than or equal to 1.

According to a preferred alternative, b is greater than or equal to 1, more particularly greater than or equal to 2, preferably greater than or equal to 4. With further preference at least 20 wt % of the olefinically functionalized siloxane oligomers, more particularly of the formula I, have a degree of oligomerization (a+b+c) of greater than or equal to 5, optionally greater than or equal to 8, with a greater than or equal to 1, and optionally b greater than or equal to 1 and optionally c greater than or equal to 1, where the fraction of siloxane oligomers with T structure is greater than or equal to ($\geq$) 5%, and preferably the viscosity is less than or equal to ($\leq$) 1000 mPa s. With further preference the fraction of T structures in the siloxane oligomers is greater than or equal to 10%, and at the same time the viscosity is less than or equal to 500 mPa s.

Particularly preferred compositions comprise siloxane oligomers, where
a) the siloxane oligomers and at least one structure of the formula I, in each case derived from alkoxysilanes of the formula II, have a vinyl group as olefinic radical A, with $R^1$ independently at each occurrence corresponding to a methyl or ethyl group,
b) the siloxane oligomers and at least one structure of the formula I, in each case derived from alkoxysilanes of the formula II, have a vinyl group as olefinic radical A, and derived from alkoxysilanes of the formula III have a propyl group as unsubstituted hydrocarbon radical B, where $R^1$ and $R^3$ independently at each occurrence correspond to a methyl or ethyl group, or
c) the siloxane oligomers and at least one structure of the formula I, in each case derived from alkoxysilanes of the formula II and formula IV and optionally of the formula III, are selected from a) or b), where $R^3$ derives from formula IV and independently at each occurrence corresponds to a methyl or ethyl group.

Likewise preferred compositions comprise, in each case independently, siloxane oligomers with derived structural elements, and optionally and at least one structure of the formula I composed of at least one olefinically functionalized alkoxysilane of the general formula II, which are selected from vinyltriethoxysilane, vinyltrimethoxysilane, and optionally of formula III, the alkoxysilanes of the formula III being selected from methyltriethoxysilane, methyltrimethoxysilane, ethyltriethoxysilane, ethyltrimethoxysilane, propyltriethoxysilane, propyltrimethoxysilane, butyltriethoxysilane, butyltrimethoxysilane, n-butyltriethoxysilane, n-butyltrimethoxysilane, isobutyltriethoxysilane, isobutyltrimethoxysilane, hexyltriethoxysilane, hexyltrimethoxysilane, n-hexyltriethoxysilane, n-hexyltrimethoxysilane, isohexyltriethoxysilane, isohexyltrimethoxysilane, octyltriethoxysilane, octyltrimethoxysilane, n-octyltriethoxysilane, n-octyltrimethoxysilane, isooctyltriethoxysilane, isooctyltrimethoxysilane, undecyltriethoxysilane, undecyltrimethoxysilane, decyltriethoxysilane, decyltrimethoxysilane, nonadecyltriethoxysilane, nonadecyltrimethoxysilane, dodecyltriethoxysilane, dodecyltrimethoxysilane, $C_{13}H_{27}$-triethoxysilane, $C_{13}H_{27}$-trimethoxysilane, $C_{14}H_{29}$-triethoxysilane, $C_{14}H_{29}$-trimethoxysilane, $C_{15}H_{31}$-trimethoxysilane, $C_{15}H_{31}$-triethoxysilane, hexadecyltriethoxysilane and hexadecyltrimethoxysilane, dimethyldimethoxysilane (DMDMO), dimethyldiethoxysilane, propylmethyldimethoxysilane, propylmethyldiethoxysilane, n-octylmethyldimethoxysilane, n-hexylmethyldimethoxysilane, n-hexylmethyldiethoxysilane, propylmethyldiethoxysilane, propylmethyldiethoxysilane, cyclohexyltriethoxysilane, n-propyltri-n-butoxysilane, hexadecylmethyldimethoxysilane and/or hexadecylmethyldiethoxysilane, and also mixtures of these silanes, or a mixture comprising at least two of the silanes, and also their transesterification products.

Further preferred compositions comprise, in each case independently, siloxane oligomers having derived structural elements and optionally at least one structure of the formula I composed of at least one olefinically functionalized alkoxysilane of the general formula II, selected from alkoxysilanes of the formula II having an olefinic radical A selected from at least one allyl, butenyl, 3-butenyl, pentenyl, hexenyl, ethylhexenyl, heptenyl, octenyl, cyclohexenyl-C1 to C8-alkylene, cyclohexenyl-2-ethylene, 3'-cyclohexenyl-2-ethylene, cyclohexadienyl-C1 to C8-alkylene and cyclohexadienyl-2-ethylene group, where $R^1$ independently at each occurrence corresponds to a methyl or ethyl group, or of at least one aforementioned olefinically functionalized alkoxysilane of the formula II, particular preference being given to the combination of a cyclohexenyl-2-ethylene- or cyclohexadienyl-2-ethylene-functionalized alkoxysilane of the formula II with an alkoxysilane of the formula III; the at least one alkoxysilane of the formula III is selected from methyltriethoxysilane, methyltrimethoxysilane, ethyltriethoxysilane, ethyltrimethoxysilane, propyltrimethoxysilane, propyltrimethoxysilane, butyltriethoxysilane, butyltrimethoxysilane, n-butyltriethoxysilane, n-butyltrimethoxysilane, isobutyltriethoxysilane, isobutyltrimethoxysilane, hexyltriethoxysilane, hexyltrimethoxysilane, n-hexyltriethoxysilane, n-hexyltrimethoxysilane, isohexyltriethoxysilane, isohexyltrimethoxysilane, octyltriethoxysilane, octyltrimethoxysilane, n-octyltriethoxysilane, n-octyltrimethoxysilane, isooctyltriethoxysilane, isooctyltrimethoxysilane, undecyltriethoxysilane, undecyltrimethoxysilane, decyltriethoxysilane, decyltrimethoxysilane, nonadecyltriethoxysilane, nonadecyltrimethoxysilane, dodecyltriethoxysilane, dodecyltrimethoxysilane, $C_{13}H_{27}$-triethoxysilane, $C_{13}H_{27}$-trimethoxysilane, $C_{14}H_{29}$-triethoxysilane, $C_{14}H_{29}$-trimethoxysilane, $C_{15}H_{31}$-trimethoxysilane, $C_{15}H_{31}$-triethoxysilane, hexadecyltriethoxysilane and hexadecyltrimethoxysilane and also the transesterification products thereof.

Additionally or alternatively to one or more of the aforementioned features, a composition of the invention, preferably after complete hydrolysis of all the alkoxy groups, has an alcohol content (VOC) of less than or equal to 20 wt %, more particularly less than or equal to 18 wt %, preferably less than or equal to 15 wt %, more preferably less than or equal to 12 wt %, including all numerical values situated in between, more particularly 19, 17, 16, 14, 13, 12, 11, 10, etc., with the proviso that the amount of water added is only as much as is needed for the hydrolysis. There is no further dilution for the determination.

Additionally or alternatively to one or more of the aforementioned features, the composition preferably has a molar ratio of A radicals to B radicals of 1:0 to 1:8, preferably of about 1:0 to 1:4, more preferably a ratio of 1:0 to 1:2, preferably 1:0 to 1:1, preferably about 1:1.

It is further preferred here if the composition comprises olefinic siloxane oligomers in which
(i) the ratio of the silicon atoms, selected from olefinically functionalized silicon atoms and from silicon atoms functionalized with a saturated hydrocarbon, to alkoxy groups in the siloxane oligomer, or alternatively in the general formula I, is from 1:0.3 to 1:2.0, more preferably 1:1.0 to 1:1.8, likewise preferred, however, are also 1:0.4 to 1:1.5, 1:0.4 to 1:1.2, preferably 1:0.4 to 1:1.1, more preferably of 1:0.4 to 1:0.9, with further preference from 1:0.4 to 1:0.8, more particularly 1:0.4 to 1:0.7, with the proviso that the olefinically functionalized siloxane oligomer derives from alkoxysilanes of the general formulae II and III,
(ii) the ratio of the silicon atoms, selected from olefinically functionalized silicon atoms and from silicon atoms functionalized with a saturated hydrocarbon, to alkoxy groups in the siloxane oligomer or alternatively in the general formula I is from 1:0.5 to 1:2.5, more particularly from 1:0.5 to 1:1.0, alternatively from 1:0.9 to 1:2.5, more particularly from 1:0.9 to 1:1.5, more particularly from 1:1.0 to 1:1.4, preferably from 1:1.0 to 1:1.3, more preferably from 1:1.0 to 1:1.2, with the proviso that the olefinically functionalized siloxane oligomer derives from alkoxysilanes of the general formulae II and IV and of the formula III.

Likewise preferably it is possible for compositions of the invention, additionally or alternatively, to have olefinically functionalized siloxane oligomers in which the ratio of M structures to D structures of the silicon atoms in the olefinically functionalized siloxane oligomers is preferably in the range from 1:1.5 to 1:10, with preferably 5% of the silicon atoms being present as T structure. Preferred ratios of M structures to D structures are from 1:2 to 1:10 with greater than or equal to 5% T structures, more particularly 1:2.5 to 1:5, such as preferably about 1:2.5; 1:3.5; 1:4.5; 1:5; 1:6; 1:7; 1:8 or else 1:9, and also all values in between.

According to one alternative, compositions of purely olefinically substituted siloxane oligomers are prepared, more particularly of the formula I with a being an integer greater than or equal to 2, with preferably at least 20 wt % of the siloxane oligomers present with a greater than or equal to 4, optionally with greater than or equal to 8. Preferred olefinic groups are linear, branched or cyclic, alkenyl, cycloalkenyl-alkylene-functional groups having in each case 2 to 16 C atoms, preferably a vinyl, allyl, butenyl, such as 3-butenyl, pentenyl, hexenyl, ethylhexenyl, heptenyl, octenyl, cyclohexenyl-C1 to C8-alkylene, preferably cyclohexenyl-2-ethylene, such as 3'-cyclohexenyl-2-ethylene and/or cyclohexadienyl-C1 to C8-alkylene, preferably cyclohexadienyl-2-ethylene group. The composition may optionally be based on a siloxane oligomer which has been prepared in the presence of tetraalkoxysilane.

In accordance with a second preferred alternative, compositions of olefinically and alkyl-substituted siloxane oligomers are prepared, more particularly of the formula I with a greater than or equal to 1 and b greater than or equal to 1, and more particularly at least 20 wt % of the siloxane oligomers have (a+b) equal to an integer greater than or equal to 4, optional greater than or equal to 8. In the case of these compositions it is further preferred if the molar ratio of A radicals to B radicals is 1:0 to 1:8, the ratio of a:b being more particularly 1:0 to 1:8, more particularly 1:0 or 1:1 to 1:8. The composition may optionally be based on a siloxane oligomer which has been prepared in the presence of tetraalkoxysilane.

In accordance with a further preferred alternative, compositions of vinyl- and alkyl-substituted siloxane oligomers are prepared, more particularly of the formula I with a greater than or equal to 1 and b greater than or equal to 1, and more particularly with 20 wt % of the siloxanes with (a+b) equal to an integer greater than or equal to 4, optionally greater than or equal to 8, preferably with a molar ratio of A radicals to B radicals of 1:0 to 1:8, more particularly of a:b of 1:0 to 1:8, more particularly 1:0 or 1:1 to 1:8. The compositions may optionally be based on a siloxane oligomer which has been prepared in the presence of tetraalkoxysilane.

With further preference the composition comprises siloxane oligomers with structural elements which are obtainable from or derived from at least one of the alkoxysilanes, from olefinically functionalized alkoxysilanes of the general formula II and optionally from alkoxysilane of the formula III functionalized with a saturated hydrocarbon radical, and optionally from a tetraalkoxysilane of the general formula IV $Si(OR^3)_4$, with preferably at least 20 wt % of the siloxane oligomers having a degree of oligomerization of (a+b+c) of greater than or equal to 4, optionally greater than or equal to 8.

A structural element—a monomeric siloxane unit—refers consistently to the individual structural unit M, D, T or Q, i.e. the structural unit which derives from an alkoxy-substituted silane and which is formed by at least partial hydrolysis to optionally complete hydrolysis and at least partial condensation in a condensate. In accordance with the invention it is possible in particular for the siloxane oligomers with the following structural elements to form, such as, preferably: $(R^1O)[(R^1O)_{1-x}(R^2)_xSi(A)O]_aR^1$; $(R^1O)[(R^1O)_{1-x}(R^2)_xSi(A)O]_a$; $[(R^1O)_{1-x}(R^2)_xSi(A)O]_a$; $[(R^1O)_{1-x}(R^2)_xSi(A)O]_aR^1$; $(R^3O)[Si(Y)_2O]_c$; $[Si(Y)_2O]_cR^3$, $(R^3O)[Si(Y)_2O]_cR^3$; $[Si(Y)_2O]_c$, $(R^3O)[Si(B)(R^4)_y(OR^3)_{1-y}O]_bR^3$; $[Si(B)(R^4)_y(OR^3)_{1-y}O]_bR^3$, $[Si(B)(R^4)_y(OR^3)_{1-y}O]_b$; $(R^3O)[Si(B)(R^4)_y(OR^3)_{1-y}O]_bR^3$, which may form catenary, cyclic and/or crosslinked structures, and in the presence of tetraalkoxysilanes or their hydrolysis and/or condensation products, it is also possible for three-dimensionally crosslinked structures to be formed. The structural elements with free valencies on the Si atom are satisfied covalently via —O—Si, and the free valencies on the O atom are satisfied with —Si-bridged bonds of other structural elements, alkyl or optionally hydrogen. These structural elements may take up a disordered or else statistical arrangement in the condensates, and this arrangement, as the skilled person is aware, may also be controlled by the sequence of the addition and by the conditions of hydrolysis and/or condensation. The general formula I does not reproduce the composition or structure that is actually present. It corresponds to one idealized possibility of representation.

The composition preferably comprises siloxane oligomers which come about through statistical and/or disordered homo- or co-hydrolysis and/or homo- or co-condensation and/or block condensation of the stated structural elements, based on the alkoxysilanes of the formulae II, III and/or IV, substituted in accordance with the invention by A or B radicals, and/or which form under the experimental conditions selected.

The substitution pattern of the structural elements is also valid, accordingly, for the catenary, cyclic, crosslinked and/or three-dimensionally crosslinked siloxane oligomers in the composition that are not represented in idealized form, it being possible for the silyl groups of the siloxane oligomers to be substituted, independently, as follows: by Y an $OR^3$ or, in crosslinked and/or three-dimensionally crosslinked structures, independently of one another, $OR^3$ or $O_{1/2}$—in a siloxane bond, with radicals A and/or B, as defined; $R^3$ corresponds in the siloxane oligomers substantially to an alkyl radical, as defined for $R^3$, and in crosslinked and/or three-dimensionally crosslinked structures it is also possible for siloxane bonds with $O_{1/2}$ to be formed, in each case independently of one another, from the radicals $OR^3$, and/or these radicals, independently of one another, may be present in the form of $O_{1/2}$, and optionally, independently, with $R^2$ and/or $R^4$, and, which as defined, correspond to an alkyl radical having 1 to 15 C atoms, with —$OR^1$; $R^1$ may likewise, as defined, be an alkyl radical having 1 to 4 C atoms.

The invention also provides a composition comprising olefinically functionalized siloxane oligomers, more particularly at least one siloxane oligomer according to the idealized formula I, comprising as further components at least one organic solvent, an organic polymer, water, salt, filler, additive, pigment or a mixture of at least two of the stated components. The components may be added during the preparation of the composition and at a later point in time to the composition.

One particular advantage of the composition of the invention is that as a result of its preparation it has a very low chloride content and hence leads to a considerable improvement in fire protection properties in the context of processing in cable compounds. It is therefore a key advantage of the composition that as a liquid-phase product, optionally after removal of the hydrolysis alcohol and any solvent added, it can be used directly in an economic way in accordance with the invention. A further advantage of the compositions of the invention is that as a result of the increased fraction of T structures and at the same time <3000 mPa s dynamic viscosity, with good processing properties in the extruder, they lead to an improved elongation at break on the part of the thermoplastics and elastomers processed with them, and also that the tensile properties have been able to be improved.

Compositions of the invention of olefinically functionalized siloxane oligomers have an alcohol content in relation to the composition, preferably of free alcohol, of less than or equal to 2 wt % to 0.0001 wt %, more particularly less than or equal to 1.8 wt %, preferably less than or equal to 1.5 wt %, more preferably less than or equal to 1.0 wt %, very preferably less than or equal to 0.5 wt % down to the detection limit. A composition has this low alcohol content, preferably free alcohol content, over at least 3 months, preferably over a period of 6 months. These low VOC contents can be ensured by the process of the invention, which provides particularly low-chlorine-content compositions of siloxane oligomers with a low alkoxy content.

One particular advantage of the process of the invention is manifested in the use of solvents in combination with acidic hydrolysis and/or condensation catalysts under conditions of homogeneous catalysis. The acidic catalysts used in accordance with the invention are soluble in the solvent, the alkoxysilanes and the siloxane oligomers prepared. Moreover, the alkoxysilanes and the siloxane oligomers are soluble in the solvent. As a result of these measures it has only now become possible, without a costly and inconvenient distillation, to obtain particularly narrow molar mass distributions in the siloxane oligomers and at the same time to obtain high-purity siloxane oligomer compositions which are virtually catalyst-free, being free more particularly of hydrolysable chlorine and/or total chloride, in the form of a liquid-phase product.

Via the addition and/or the amount added of solvent, preferably alcohol, it is possible, together with the amount of water, to set the molecular weight and the molecular weight distribution in an optimum way and in so doing largely to prevent formation of high molecular mass oligomers. The unwanted oligomers of relatively high molecular mass are formed only at a very low level.

A further aspect of the composition of the invention and of the process of the invention is that the process operates without the use of basic catalysts, more particularly nitrogen-containing compounds, or of acidic sulphur-containing ion exchangers. Both catalysts lead to conditions of heterogeneous catalysis. Thus, for example, aqueous ammonia leads to the formation of emulsions, and reaction over ion exchangers containing sulphonic acid groups or sulphuric acid groups also bring about conditions of a heterogeneous catalysis. It has been found that the conditions of a heterogeneous catalysis are not suitable for producing the desired narrow molar mass distribution of siloxane oligomers. Consequently, the compositions of the invention are free from acidic sulphur-containing groups, more particularly sulphuric acid groups or sulphonic acid groups, and/or free from nitrogen-containing compounds, more particularly from nitrogen-containing compounds which are introduced via basic catalysts. In the process of the invention it is also possible to do without the use of metal oxides, optionally in combination with an acid; consequently, the compositions of the invention are free from metallic residues introduced through the addition of metal oxides, such as, more particularly, copper oxides, iron oxides, aluminium oxides, copper halides, iron halides, copper hydroxide, iron hydroxide, aluminium hydroxide. Compositions of the invention therefore preferably contain only metals that are intrinsically present, the metal content being preferably less than 0.001 wt % to 0.1 ppm by weight. Correspondingly, in the process of the invention, it is possible to forgo the addition of basic compounds, such as calcium carbonate for the neutralization. The compositions of the invention consequently contain no additionally added calcium, and preferably they contain less than or equal to 1 wt %, more particularly less than or equal to 0.1 wt % to 0.1 ppm by weight, of calcium. The compositions and processes are therefore free from nitrogen-containing compounds, calcium-containing compounds, free from metal-containing compounds, more particularly metal oxides, and free from sulphur-containing compounds, more particularly acidic sulphur compounds.

Likewise provided by the invention is a process for preparing a composition comprising olefinically functionalized siloxane oligomers, and also, in particular, compositions obtainable by this process, by reacting (i) (at least) an olefinically functionalized alkoxysilane of the general formula II, $$A\text{-}Si(R^2)_x(OR^1)_{3-x} \tag{II},$$

where in formula II A corresponds to an olefinic radical selected more particularly from a linear, branched or cyclic alkenyl- or cycloalkenyl-alkylene-functional group having in each case 2 to 16 C atoms, $R^2$ independently corresponds to a linear, branched or cyclic alkyl radical having 1 to 15 C atoms and x is 0 or 1, and $R^1$ independently corresponds to a linear, branched and/or cyclic alkyl radical having 1 to 4 C atoms, (ii) in the presence of a hydrolysis and/or condensation catalyst, more particularly of HCl, saturated or unsaturated organic acids, such as formic acid or acetic acid, and/or fatty acids, for example myristic acid, and/or polyfunctional organic acids, such as citric acid, fumaric acid, (i.1) optionally with (at least) an alkoxysilane of the formula III,

$$B\text{—}Si(R^4)_y(OR^3)_{3-y} \quad (III),$$

where in formula III B corresponds to a saturated hydrocarbon radical, $R^3$ corresponds independently at each occurrence to a linear, branched and/or cyclic alkyl radical having 1 to 4 C atoms, and $R^4$ corresponds to a linear, branched or cyclic alkyl radical having 1 to 15 C atoms, and y is 0 or 1, and (i.2) optionally with (at least) a tetraalkoxysilane of the formula IV, where in formula IV $R^3$ independently at each occurrence is a linear, branched and/or cyclic alkyl radical having 1 to 4 C atoms,

$$Si(OR^3)_4 \quad (IV),$$

and (iii) with a defined amount of water of greater than or equal to 1.1 to 1.59 mol, preferably 1.0 to 1.5 mol, of water per mole of silicon atoms in the alkoxysilanes used, i.e. at least of the formula I and optionally additionally selected from the formulae III and IV, optionally in the presence of a solvent, preferably alcohol, to give oligomers, in particular with x=0 and y=0, and (iv) substantially removing the hydrolysis alcohol and the solvent that is optionally present, and obtaining more particularly a composition comprising a siloxane oligomer, (v) more particularly with a chlorine content, more particularly total chloride content, of less than or equal to 250 mg/kg, more particularly less than or equal to 150 mg/kg, preferably less than or equal to 100 mg/kg, more preferably less than or equal to 75 mg/kg, with further preference less than or equal to 50 mg/kg, with additional preference less than or equal to 35 mg/kg, the hydrolysable chloride content being preferably less than or equal to 8 mg/kg, preferably less than or equal to 5 mg/kg, and (vi) where greater than or equal to 10% of the silicon atoms in the olefinically functionalized siloxane oligomer, in relation to the sum total of silicon atoms in the siloxane oligomer, are present as T structure, and optionally (vii) where the composition comprising olefinically functionalized siloxane oligomers is recovered or obtained as liquid-phase product.

Advantageously, following step (iv) or preferably as the last measure in step (iv), the composition is obtained or recovered. The composition is preferably in the form of a liquid-phase product. In accordance with the invention the composition is recovered as the liquid-phase product, optionally following removal of the hydrolysis alcohol and any added solvent.

According to one preferred alternative, (i) the at least one alkoxysilane of the formula II is reacted in step (ii), in the presence of a hydrolysis and/or condensation catalyst, with (i.1) at least one alkoxysilane of the formula III. According to a further preferred alternative, (i) the at least one alkoxysilane of the formula II is reacted in step (ii) in the presence of a hydrolysis and/or condensation catalyst with (i.2) at least one alkoxysilane of the formula IV. According to a further preferred alternative, (i) the at least one alkoxysilane of the formula II is reacted in step (ii), in the presence of a hydrolysis and/or condensation catalyst, with (i.1) at least one alkoxysilane of the formula III and (i.2) at least one alkoxysilane of the formula IV. Judiciously it is also possible in (iii) to use, as a defined amount of water, greater than or equal to 1.0 to 1.6 mol of water per mole of silicon atoms in the alkoxysilanes used.

Likewise provided by the invention is a process for producing a composition comprising olefinically functionalized siloxane oligomers, and also, in particular, compositions obtainable by this process, with the steps (i), (ii), (iii) and (iv) and optionally (i.1) and/or (i.2), to give a composition comprising olefinically functionalized siloxane oligomers as per (vi), with in particular greater than or equal to 10% of the silicon atoms in the olefinically functionalized siloxane oligomer being present, in relation to the sum total of silicon atoms in the siloxane oligomer, as T structure, and (vii) where the composition comprising olefinically functionalized siloxane oligomers is recovered as the liquid-phase product following step (iv) or (v). The chlorine content obtainable in the composition is, according to this variant embodiment of the process, only optionally less than or equal to 250 mg/kg. Compositions according to this variant embodiment feature the aforementioned molar mass distributions described, independently of the chlorine content, and in particular also exhibit the stated TGA values. Accordingly, the invention likewise provides compositions of olefinic siloxane oligomers, independently of the chlorine content or total chloride content, which greater than or equal to 85%, preferably 90% (area %, GPC), have a molecular weight (Mw) of less than 1000 g/mol. In particular in combination with an Mw of greater than or equal to 30% (area %, GPC, Mw) of 500 to 750 (rel. Mw), greater than or equal to 30% to less than or equal to 50% preferably have an Mw of 500 to 750, more preferably greater than or equal to 35% to less than or equal to 45%. All figures should always be understood in relation to the overall composition.

According to one preferred embodiment, an alkenyl-functionalized alkoxysilane of the general formula II is reacted optionally together with an alkylalkoxysilane of the general formula III in the presence of a condensation catalyst. With further preference one alkenyltrialkoxysilane and optionally an alkyltrialkoxysilane are reacted in each case. The reaction may take place optionally in the presence of a solvent, preference being given to using the corresponding alcohol of the alkoxysilane. In the process of the invention it is possible with particular advantage to use 0.001 to 5 volume units of the corresponding alcohol per volume unit of alkoxysilane, more particularly trialkoxysilane. Further preference is given to using 0.25 to 1 volume units per volume unit of trialkoxysilane.

According to one particularly preferred process variant, reaction takes place in step (iii) with a defined amount of water in the presence of an alcohol in an amount of in each case 0.05 to 2.5 volume units of alcohol per volume unit of alkoxysilane, more particularly with 0.1 to 2.0 volume units of alcohol per volume unit of alkoxysilane, preferably 0.2 to 1.5, more preferably 0.2 to 1.0 or 0.2 to 0.9. Preferably 0.5 plus/minus 0.4 volume units of alcohol per volume unit of alkoxysilane. Preferably in this context, in the case of a reaction of VTMO or VTEO, for the dilution plus metering, 0.5 to 2.5, 0.5 to 2.0, and/or in step (iv) at least once during step (iv), or subsequently, a defined amount of alcohol are added further and removed. For the further addition in (iv) or subsequently, it is likewise possible multiply to meter in 0.001 to 5 volume units, more particularly 0.1 to 2.5 volume units, of alcohol per volume unit of alkoxysilane. These measures may be repeated arbitrarily, preferably 1 to 10 times, more preferably 1 to 5 times. The alcohol distilled off beforehand, particularly after a purification procedure, can be used again for the removal of chlorides and water. This may take place preferably in step (30.i), in which at least once, preferably two to six times, during the distillative working-up, a defined amount of alcohol is added, as elucidated below.

Alternatively it is possible with preference to use 1.0 to 1.5 mol of water per mole of silicon atoms in the alkoxysilanes used.

In accordance with the invention the catalysts used as hydrolysis and/or condensation catalyst are acidic catalysts which are gaseous under standard conditions, more particularly HCl, and which may be dissolved in aqueous phase or alcoholic phase.

The solvent used and/or the alcohol used are anhydrous; more particularly, the solvent or the alcohol is used with a water content of less than or equal to 1 ppm by weight. In the case of solvents containing water, this water content must be taken into account in the reaction.

As olefinically functionalized alkoxysilane, preference is given to using a silane of the general formula II,

$$A\text{-}Si(R^2)_x(OR^1)_{3-x} \quad (II)$$

where A is a linear, branched or cyclic alkenyl- or cycloalkenyl-alkylene-functional group having in each case 2 to 18 C atoms, more particularly having 2 to 16 C atoms, preferably having 2 to 8 C atoms, more preferably an alkenyl group having one to two double bonds, preferably a vinyl, allyl, butenyl, pentenyl, hexenyl, ethylhexenyl, heptenyl, octenyl, cyclohexenyl-C1 to C8-alkylene, preferably cyclohexenyl-2-ethylene, such as 3'-cyclohexenyl-2-ethylene, and/or cyclohexadienyl-C1 to C8-alkylene, very preferably a cyclohexadienyl-2-ethylene group, x more particularly being 0, and $R^1$ independently is a linear, branched and/or cyclic alkyl radical having 1 to 4 C atoms, more particularly a methyl, ethyl or propyl group.

Used preferably as alkoxysilane of the formula III is an alkoxysilane with an unsubstituted hydrocarbon radical B,

$$B\text{—}Si(R^4)_y(OR^3)_{3-y} \quad (III)$$

which is a linear, branched or cyclic alkyl radical having 1 to 16 C atoms, more particularly a methyl, ethyl, propyl, isobutyl, octyl or hexadecyl group. And $R^2$ and $R^4$ may be independently of one another, in formulae II and III, preferably methyl, ethyl, propyl, butyl, pentyl, hexyl, cyclohexyl, heptyl, octyl, nonyl and also further alkyl groups known to the skilled person, including the structural isomers. One preferred alkoxysilane of the formula III has an unsubstituted hydrocarbon radical B selected from a methyl, ethyl, propyl, butyl, isobutyl, n-butyl, tert-butyl, pentyl, n-pentyl, isopentyl, neopentyl, hexyl, isohexyl, neohexyl, 2,2-dimethylbutyl, 2,3-dimethylbutyl, 2-methylpentyl, 3-methylpentyl, heptyl, octyl, n-octyl, isooctyl, nonyl, decyl, undecyl, dodecyl, $C_{13}H_{27}$, $C_{14}H_{29}$, $C_{15}H_{31}$ and hexadecyl group, with y being 0 or 1, $R^4$ being a linear, branched or cyclic alkyl radical having 1 to 15 C atoms, as defined above, and $R^3$ independently being a methyl, ethyl or propyl group. According to one alternative preferred embodiment, unsubstituted hydrocarbons having branched and/or cyclic alkyl radicals with 3 to 16 C atoms are employed as radical B. According to another preferred alternative of the invention, linear alkyl radicals having 1 to 7 C atoms are used as unsubstituted hydrocarbon radical B.

Likewise provided by the invention are processes in which, in the olefinically functionalized alkoxysilane of the general formula II, x is 0, and, optionally, in the alkoxysilane of the formula III functionalized with a saturated hydrocarbon radical, y is 0. Alternatively x can be 0 and y can be 1, or x can be 1 and y can be 0.

There is at least partial hydrolysis, and in particular at least partial co-condensation; preferably, the condensable, partially hydrolysed alkoxysilanes are subjected to substantially complete condensation. With particular preference, partial hydrolysis and condensation take place only to the extent desired for the preparation of the oligomers with a preferred degree of oligomerization.

In accordance with the invention the hydrolysis alcohol is removed, preferably by distillation, and the composition of the invention is obtained. Particularly gentle distillation of the hydrolysis alcohol and/or the solvent takes place under reduced pressure. Depending on procedure, a particularly economic process can be carried out without the addition of a solvent. In accordance with the invention, the composition prepared in this way, following removal of the hydrolysis alcohol and any solvent, does not itself have to be purified further, and more particularly does not itself have to be distilled, in order to be suitable for the uses according to the invention. Depending on preparation procedure, the composition may optionally be filtered or decanted following removal of the hydrolysis alcohol. The process of the invention is therefore very much more economic than known processes where the oligomer, in order to be suitable for further application, must be purified by distillation.

The invention also provides a process in which, in each case independently, the at least one olefinically functionalized alkoxysilane of the general formula II is selected from vinyltriethoxysilane, allyltriethoxysilane, butenyltriethoxysilane, pentenyltriethoxysilane, hexenyltriethoxysilane, ethylhexenyltriethoxysilane, heptenyltriethoxysilane, octenyltriethoxysilane, cyclohexenyl-C1 to C8-alkylenetriethoxysilane, cyclohexenyl-2-ethylenetriethoxysilane, 3'-cyclohexenyl-2-ethylenetriethoxysilane, cyclohexadienyl-C1 to C8-alkylenetriethoxysilane, cyclohexadienyl-2-ethylenetriethoxysilane, vinyltrimethoxysilane, allyltrimethoxysilane, butenyltrimethoxysilane, pentenyltrimethoxysilane, hexenyltrimethoxysilane, ethylhexenyltrimethoxysilane, heptenyltrimethoxysilane, octenyltrimethoxysilane, cyclohexenyl-C1 to C8-alkylenetrimethoxysilane, cyclohexenyl-2-ethylenetrimethoxysilane, 3'-cyclohexenyl-2-ethylenetrimethoxysilane, cyclohexadienyl-C1 to C8-alkylenetrimethoxysilane and cyclohexadienyl-2-ethylenetrimethoxysilane, and, in each case independently, the at least one alkoxysilane of the formula III is selected independently at each occurrence from methyltriethoxysilane, ethyltriethoxysilane, n-propyltriethoxysilane, isopropyltriethoxysilane, butyltriethoxysilane, n-butyltriethoxysilane, isobutyltriethoxysilane, hexyltriethoxysilane, n-hexyltriethoxysilane, isohexyltriethoxysilane, heptyltriethoxysilane, octyltriethoxysilane, n-octyltriethoxysilane, isooctyltriethoxysilane, undecyltriethoxysilane, decyltriethoxysilane, nonadecyltriethoxysilane, dodecyltriethoxysilane, $C_{13}H_{27}$-triethoxysilane, $C_{14}H_{29}$-triethoxysilane or $C_{15}H_{31}$-triethoxysilane, hexadecyltriethoxysilane, methyltrimethoxysilane, ethyltrimethoxysilane, n-propyltrimethoxysilane, isopropyltrimethoxysilane, butyltrimethoxysilane, n-butyltrimethoxysilane, isobutyltrimethoxysilane, hexyltrimethoxysilane, n-hexyltrimethoxysilane, isohexyltrimethoxysilane, heptyltrimethoxysilane, octyltrimethoxysilane, n-octyltrimethoxysilane, isooctyltrimethoxysilane, undecyltrimethoxysilane, decyltrimethoxysilane, nonadecyltrimethoxysilane, dodecyltrimethoxysilane, $C_{13}H_{27}$-trimethoxysilane, $C_{14}H_{29}$-trimethoxysilane or $C_{15}H_{31}$-trimethoxysilane and hexadecyltrimethoxysilane, and also, optionally, transesterification products, and, in each case independently, the alkoxysilane of the formula IV is selected from tetraethoxysilane and tetramethoxysilane. And also their esterification products comprising ethoxy groups and methoxy groups.

In accordance with the process of the invention, a composition comprising siloxane oligomers is obtained which, after implementation of steps i, ii, iii and iv and also, optionally, of steps i.1 and/or i.2, already has the inventive low chlorine content, more particularly total chloride content, of less than or equal to 250 mg/kg, more particularly less than or equal to 150 mg/kg, preferably less than or equal to 100 mg/kg, more preferably less than or equal to 75 mg/kg, with further preference less than or equal to 50 mg/kg, with additional preference less than or equal to 35 mg/kg, the hydrolysable chloride content being preferably less than 8 mg/kg, preferably less than or equal to 5 mg/kg, and where preferably greater than or equal to 5% of the silicon atoms in the olefinically functionalized siloxane oligomer, in relation to the sum total of silicon atoms in the siloxane oligomer, are present as T structure.

The reaction in the presence of a defined amount of water of greater than 1.0 mol of water per mole of silicon atom takes place preferably with a defined amount of water of greater than or equal to 1.05 to 1.60 mol of water per mole of silicon atoms in the alkoxysilanes of the formula II used and optionally at least one silane of the formula III and/or of the formula IV, more particularly with 1.1 to 1.58 mol of water, preferably greater than or equal to 1.2 to 1.58 mol of water, more preferably greater than or equal to 1.25 to 1.57 mol of water per mole of silicon atoms in the alkoxysilanes of the formula II used and optionally of the formula III and/or of the formula IV. Likewise considered to have been disclosed here are all of the numerical values for mol of water that are included within the disclosed range, more particularly down to the second decimal place, such as 1.06; 1.07; 1.08; 1.09; 1.11; 1.12; 1.13; 1.14; 1.15; 1.16; 1.17; 1.18; 1.19; 1.21; 1.22; 1.23; 1.24; 1.26; 1.27; 1.28; 1.29; 1.30; 1.31; 1.32; 1.33; 1.34; 1.35; 1.36; 1.37; 1.38; 1.39; 1.40; 1.41; 1.42; 1.43; 1.44; 1.45; 1.46; 1.47; 1.48; 1.49; 1.50; 1.51; 1.52; 1.53; 1.54; 1.55; 1.56. The water is preferably fully demineralized. To the skilled person it is clear that the water may be introduced initially, added in portions, added continuously or added together with one or all the silanes to the process. The water is preferably metered continuously or with at least one interruption over a period of less than 1 minute to 100 minutes, and the reaction of the alkoxysilanes is preferably carried out at reaction temperatures in the range of preferably 40° C. to 80° C., more preferably in the range from 50° C. to 80° C., more particularly at a pH of less than 7. The water contents of added solvents, such as alcohol, must be taken into account, as water, in the process.

Generally speaking, the water or an amount of water, according to point/step iii of the process (29.i, cf. Claim 29), can be metered in continuously or at least with an interruption over a period of 1 to 1000 minutes and a temperature in the reaction mixture of 5 to 90° C. can be set, more particularly 37 to 88° C., preferably 40 to 85° C., more preferably 45 to 83° C., with further preference 50 to 80° C., the pH preferably being less than or equal to 7; optionally, the water is added together with the catalyst and optionally with a solvent, more particularly with an alcohol. The reaction may then take place preferably such that (29.ii, cf. Claim 29) this mixture from (29.i, cf. Claim 29), i.e. reaction mixture, is treated and/or further reacted optionally for at least 10 minutes to 36 hours, more particularly from 10 minutes to 8 hours (h), at 5 to 80° C., preferably at 40 to 80° C., preferably with mixing, and optionally the reaction mixture may also continue reacting in the course of cooling. To adjust the molecular weight, an alkoxytrialkylsilane, more particularly alkoxytrimethylsilane, can be added to the process. The composition obtained in this way can then be decanted or heated for distillative removal of the alcohol, such as the hydrolysis alcohol. From this crude product, the alcohol, optionally including a catalyst, more particularly HCl, is preferably removed by distillation with heating under reduced pressure.

According to one preferred embodiment, in the process according to point iv, the hydrolysis alcohol and the solvent optionally present, more particularly the added alcohol, are removed by distillation and preferably (30.i, cf. Claim 30) at least once, preferably two to six times, during the distillative working-up, a defined amount of alcohol is added, and/or (30.ii, cf. Claim 30) before or during the distillative removal of the hydrolysis alcohol and of the solvent optionally present, more particularly of the alcohol, a defined amount of a reducing agent, more particularly an inorganic reducing agent, such as alkali metal, alkaline earth metal, aluminium or a metal hydride, or a base, such as preferably HMDS or another amine or an alkali metal alkoxide, is added, and subsequently the olefinically functionalized siloxane oligomer, which is present as the liquid-phase product, is filtered or decanted, and/or the olefinic siloxane oligomer is contacted with an ion exchanger.

According to the first alternative, precipitates or flocs formed by the filtering and/or decanting can be removed substantially from the composition comprising the siloxane oligomer. Preferably a defined amount of a reducing agent is added, more particularly an inorganic reducing agent, very preferably a metallic reducing agent, such as alkali metal, preferably sodium, or used as alkaline earth metal, preferably magnesium or calcium, or aluminium, and as metal hydride, preferably Li aluminium hydride, aluminium hydride, or as base preferably gaseous ammonia, LDA (Li diisopropylamide), Li isopropylhexylamide, hexamethyldisilazane, and as alkali metal alkoxide, such as Na or K methoxide or Na or K ethoxide, or alkali metal alkylate, such as butyl-Li. It is also possible for metal hydrides known to the skilled person, such as NaH, or else lithium aluminium hydride, or bases which form low-solubility precipitates with the hydrogen chloride, to be used additionally in the process in order to achieve a further reduction in the amount of chlorine (or chloride) in the composition. Bases suitable for the process ought to form no water in a reaction with the catalyst, e.g. HCl, or with organically bonded chlorine, such as Cl—Si.

The alcohol already present and/or alcohol formed in the reaction is removed substantially, preferably completely, from the reaction mixture in all process variants according to the invention. The distillative removal of the alcohol is carried out preferably under reduced pressure. This distillative removal of the alcohol corresponds to the working-up of the composition, since after this step the composition comprising siloxane oligomers is recovered or obtained with a defined total amount of chloride, more particularly in the form of liquid-phase products, and is preferably obtained with a defined polydispersity, preferably with D=1.10 to 1.42, more preferably D=1.10 to 1.21, especially for siloxanes derived from alkoxysilanes of the formula II. Alternatively, for siloxanes derived from alkoxysilanes of the formula II and III, the polydispersity D may be 1.20 to 1.43. The distillative removal of the alcohol is carried out preferably until the temperature obtained at the top of the column corresponds to the boiling temperature of water or to that of the siloxane oligomers. Alternatively until an alcohol content is found of less than or equal to 1.0 wt %, preferably less than or equal to 0.5 wt %. Generally speaking, the resulting composition of the invention is then substantially solvent-free, more particularly alcohol-free. The composition obtained in this way preferably corresponds directly to the composition of the invention, and with preference need not itself be purified further.

The process of the invention can be operated batchwise or continuously. Before or else after the removal of the alcohol, the composition may be admixed with at least one processing assistant such as silicone oil, such as polydimethylsiloxane, paraffin, liquid paraffin, or a mixture comprising one of these processing assistants.

According to one preferred variant of the process, the alkoxysilanes of the general formulae II, III and/or IV are subjected to at least partial hydrolysis and condensation in the presence of an acidic catalyst, more particularly with hydrogen chloride. Where necessary the hydrolysis and condensation may also take place in the presence of HCl and a cocatalyst. Co-catalysts contemplated include fatty acids. Alternatively it is also possible for HCl and saturated or unsaturated organic acids, such as formic acid, acetic acid, and/or fatty acids, optionally also myristic acid, and/or polyfunctional organic acids, such as citric acid, or fumaric acid, to be used as catalyst or as co-catalyst with HCl.

It is further preferred in accordance with the process for the silane of the formula II and the silane of the formula III to be used in a ratio of 1:0 to 1:8 and/or for the silane of the formula II to be used in a ratio to the silane of the formula IV of 1:0 to 1:0.22, preferably 1:0 to 1:0.20, more particularly 1:0 to 1:0.15, likewise preferably 1:0 to 1:0.10, more preferably 1:0 to 1:0.05, the silane of the formula II and the silane of the formula III being used preferably in a ratio of about 1:0 or approximately in a ratio of 1:1 or in a ratio of 1:0 to 1:2, preferably 1:0 to 1:1. Alternatively preferred is also a process in which the silane of the formula II and the silane of the formula IIII are used in a ratio of 1:0 to 1:2, preferably about 1:1, and/or the silane of the formula II is used in a ratio to the silane of the formula IV of 1:0 to 1:0.20, preferably 1:0 to 1:0.10, more preferably 1:0 to 1:0.5, likewise preferably in a ratio of 1:0.10 to 1:0.05 or about 1:0.1. The siloxane oligomers produced in the stated ratios exhibit properties which are particularly homogeneous in performance terms; the silane of the formula IV is used preferably for greater crosslinking in the oligomer or else of the oligomer with a substrate.

With particular preference, according to one alternative, the silane of the formula II and the silane of the formula III are used approximately in a ratio of 1:1; according to a further preferred alternative, the silane of the formula II and the silane of the formula IV are used in a ratio of approximately 1:0.1.

According to one embodiment, an inventive reaction is carried out of the olefinically functionalized alkoxysilane of the formula II, and optionally of the silanes III and/or IV, with a hydrolysis and condensation catalyst, in the presence of a defined amount of water of greater than 1.0 to 1.6 mol of water per mole of silicon atoms in the alkoxysilanes, and with 0.2 to 8 times the amount by weight of alcohol in relation to the amount by weight of silanes employed. According to one alternative, it is also possible for 0.0001 to 5 volume units of alcohol to be added per volume unit of silane of the formulae II, III and/or IV. Preference is given to using just a small amount by weight of alcohol, of 0.2 to 0.6, more preferably of 0.2 to 0.5, in the process of the invention, in relation to the silanes of the formula II, III and/or IV.

Preferred alcohols correspond to the hydrolysis alcohol formed by the at least partial hydrolysis and/or condensation. They include ethanol or methanol. To the skilled person it is clear that the reaction can also be carried out in the presence of another customary solvent, preference being given to those which can be distilled off easily and preferably completely—these may be, for example but not conclusively, ethers, ketones, hydrocarbons or esters. Useful solvents may alternatively be ethyl acetate, THF, ketones, ethers or hydrocarbons. To the skilled person it is clear that for reasons of business and economy an alcohol is used as solvent that is also formed as hydrolysis alcohol. Mixtures of alcohols may therefore also be used in principle. In all process variants, the solvent and the alcohol formed in the reaction are preferably removed by distillation from the reaction mixture.

According to a further preferred process variant, the degree of oligomerization of at least 20 wt % of the siloxane oligomers with n as the number of silicon atoms is set such that for them n is greater than or equal to 4, optionally greater than or equal to 8. With further preference, by the process of the invention, in particular more than 5% of the olefinically functionalized silicon atoms are obtained as T structure; preferably, this may also be more than 7.5%, preferably greater than 10%, more preferably greater than 11% or else greater than 15% and also above 22%; additionally or alternatively preferably more than 5% of the silicon atoms in the siloxane oligomer that are functionalized with a saturated hydrocarbon are also present as T structure.

In the process of the invention, the viscosity of the composition is set preferably at less than or equal to 1000 mPa s, more preferably at less than or equal to 740 mPa s, very preferably at less than or equal to 500 to about 5 mPa s.

Further, in the process, the composition comprising olefinic siloxane oligomers, more particularly the liquid-phase product, preferably after the distillative removal of the solvent and/or alcohol, can be contacted with an ion exchanger, more particularly an anion exchanger, preferably an amine-functional ion exchanger, in order to reduce further the chloride content. In this process step it is advantageous that this measure, in contrast to a distillation, does not alter the degree of oligomerization and/or the degree of branching of the product. In the case of a distillation there would automatically be a separation of the siloxane oligomer into low, medium and high boilers (liquid phase). Through the use of the ion exchanger in accordance with the invention, the degree of oligomerization of the siloxane oligomers remains the same, and the chloride content can be lowered further. Through the contacting with an ion exchanger, the chloride content or chlorine content in weight ppm of the olefinic siloxane oligomers can be reduced preferably by at least 80% in relation to the siloxane oligomers supplied to the ion exchanger. With further preference, the amount of chlorine in weight ppm of the olefinic siloxane oligomers in relation to those supplied is reduced by at least 85%, preferably by at least 90%, more preferably at least by 92%, with further preference at least by 95%, and with even more preference by at least 98%. Depending on the olefinically functionalized siloxane oligomer, and depending on the initial concentration of chlorine, the flow rate and the contact time with the anion exchanger, the chlorine content can be lowered preferably to less than or equal to 100 mg/kg, preferably to less than or equal to 50 mg/kg, more preferably to less than or equal to 25 mg/kg.

In the case of olefinically functionalized siloxane oligomers containing chlorine, i.e. with hydrolysable chlorine, more particularly chlorine-functional alkylalkoxysilanes and/or alkylalkoxysilanes with HCl, the hydrolysable chloride content can be reduced, preferably at flow rates of 0.01 m/h to 15 m/h, preferably up to 5 m/h, more particularly at up to 2.5 m/h, by at least 80%, more particularly by at least 85%, preferably by at least 90%, more preferably at least by 92%, with further preference at least by 95%, and with even further preference by at least 98%; in this case, in particular, the olefinically functionalized siloxane oligomers are not condensed further, and the anion exchanger column preferably has a diameter of 3 cm and a height of 15 cm. Very good results in diminishing hydrolysable chlorine, of up to 80%, are also obtained at flow rates of up to 10 m/h.

In the process of the invention, the anion exchanger has a carrier polymer with quaternary alkylammonium groups and/or with tertiary dialkylamino groups, the quaternary alkylammonium groups in particular having essentially hydroxide ions as counterions, and/or the tertiary dialkylamino groups being in the form of the free base.

It is particularly preferred in this context if the basic anion exchanger is a styrene-divinylbenzene copolymer having trialkylammonium groups, more particularly in the OH form, and/or a styrene-divinylbenzene copolymer having dialkylamino groups in the form of the free base. When using basic anion exchangers with a styrene-divinylbenzene copolymer having trialkylammonium groups in the chloride form, the chlorides are converted into the OH form prior to use, using an alkali metal hydroxide solution, for example. Alkali metal hydroxide solutions used are preferably aqueous solutions of potassium hydroxide, sodium hydroxide or else other bases soluble in water or aqueous alcohol, such as ammonia or alkali metal carbonates, such as $Na_2CO_3$. After the conversion of the anion exchanger into the OH form, before the contacting with the olefinic siloxane oligomers, the anion exchanger is rinsed with an alcohol, in order in particular to displace excess water. Alcohol used is preferably the alcohol which would be formed by hydrolysis of the respective alkoxy groups. In the case of methoxy groups, methanol, or ethanol in the case of ethoxy groups in the alkoxysilane.

Quaternary ammonium groups include not only alkylammonium but also N-alkyl-imine-functional groups, such as N-alkylpyridinium groups. Suitable alkyl groups contain 1 to 20 C atoms, preferably with 1 to 4 C atoms, and are preferably methyl or ethyl groups. In accordance with the invention the weakly basic anion exchangers are loaded with hydroxide ions and in particular they have nitrogen-containing groups.

In accordance with the invention it is preferable, further, if the alkoxysilanes of the formulae II, III and/or IV are subjected to at least partial hydrolysis and condensation in the presence of the defined amount of water and of a hydrolysis and condensation catalyst, such as a mineral acid, for example, such as HCl, an organic saturated or unsaturated carboxylic acid, such as formic acid and/or fatty acid, and the alcohol, more particularly both the hydrolysis alcohol and any added alcohol, is preferably removed. The hydrolysis alcohol and/or the added alcohol correspond to the free alcohol. With particular preference the amount of free alcohol in the overall composition is less than 2 wt % to 0.01 wt %, more particularly less than 2 wt % to 0.01 wt %, very preferably less than or equal to 1 wt % to 0.01 wt % down to the detection limit.

It has surprisingly emerged that the functional siloxane oligomers obtained by the process of the invention, in view of the further reduction in the chlorine content, are significantly more stable with respect to a hydrolysis, despite the fact that, in contrast to hitherto, they are no longer distilled at cost and inconvenience. As a result, the siloxane oligomers of the invention prove to be more stable than known oligomers, and at the same time their VOC content is reduced relative to the prior art oligomers.

The content of solvents, such as VOC, more particularly the free alcohol content, that is stable over a period of 3 to 6 months, in relation to the overall composition, is preferably less than or equal to 2 wt %, more particularly less than or equal to 1 wt %, very preferably less than or equal to 0.4 wt %, preferably less than or equal to 0.3 wt %.

Compounds of the formula II which can be used in the process of the invention are as follows: Vinyltriethoxysilane (VTEO), vinyltrimethoxysilane (VTMO), allyltriethoxysilane, allyltrimethoxysilane, butenyltriethoxysilane, butenyltrimethoxysilane, cyclohexenyl-alkylene-trimethoxysilane, more particularly cyclohexenyl-2-ethylene-trimethoxysilane, cyclohexenyl-2-ethylene-triethoxysilane, more preferably 3'-cyclohexenyl-2-ethylene-triethoxysilane and/or 3'-cyclohexenyl-2-ethylene-trimethoxysilane, cyclohexenedienyl-alkylenetriethoxysilane, hexenyltriethoxysilane, hexenyltrimethoxysilane, ethylhexenyltrimethoxysilane, ethylhexenyltriethoxysilane, octenyltriethoxysilane, octenyltrimethoxysilane, particular preference being given to the methoxy-substituted compounds.

Alkylalkoxysilane compounds of the formula III that can be used with preference are as follows: Compounds of the formula III with y=0 or 1, where B corresponds to a linear or branched alkyl radical having 1 to 18 C atoms, more particularly having 1 to 8 C atoms, preferably to a methyl, ethyl, more preferably n-propyl, isopropyl, butyl, pentyl, hexyl, heptyl, octyl, hexadecyl or octadecyl radical, $R^4$ corresponds to a linear, branched or cyclic alkyl radical having 1 to 15 C atoms, more particularly having 1 to 8 C atoms, preferably to a methyl, ethyl, more preferably n-propyl, isopropyl and/or octyl radical, $R^3$ corresponds to a linear and/or branched alkyl radical having 1 to 3 C atoms, more preferably to a methyl, ethyl and/or isopropyl or n-propyl radical. With particular preference B is a methyl, ethyl, propyl, octyl, hexadecyl or octadecyl radical and $R^4$ is a methyl or ethyl radical, and $R^1$ is a methyl or ethyl radical, particular preference being given to the methoxy-substituted compounds. Preferred compounds of the formula III, stated by way of example, are as follows: Methyltrimethoxysilane, methyltriethoxysilane (MTES), propyltrimethoxysilane (PTMO), dimethyldimethoxysilane (DMDMO), dimethyldiethoxysilane, propylmethyldimethoxysilane, propylmethyldiethoxysilane, n-propyltrimethoxysilane, n-propyltriethoxysilane (PTEO), n-octylmethyldimethoxysilane, n-hexylmethyldimethoxysilane, n-hexylmethyldiethoxysilane, propylmethyldiethoxysilane, propylmethyldiethoxysilane, propyltriethoxysilane, butyltrimethoxysilane, isobutyltrimethoxysilane, isobutyltriethoxysilane, octyltrimethoxysilane, octyltriethoxysilane, n-octyltrimethoxysilane, n-octyltriethoxysilane, isooctyltrimethoxysilane, isooctyltriethoxysilane, n-hexyltriethoxysilane, cyclohexyltriethoxysilane, n-propyltri-n-butoxysilane, n-propyltrimethoxysilane, n-propyltriethoxysilane, hexadecyltriethoxysilane, hexadecyltrimethoxysilane, octadecyltriethoxysilane, octadecyltrimethoxysilane, octadecylmethyldiethoxysilane, octadecylmethyldimethoxysilane, hexadecylmethyldimethoxysilane and/or hexadecylmethyldiethoxysilane, and also mixtures of these silanes, or a mixture comprising at least two of the aforementioned silanes.

Particularly preferred combinations of compounds of the formulae II, III and/or IV for preparing the olefinically functionalized siloxane oligomers, and/or the olefinically functionalized siloxane oligomers obtainable therefrom, are: Reacted in accordance with the process are in each case the compounds enclosed below by semi-colons: vinyltriethoxysilane; vinyltrimethoxysilane; vinyltriethoxysilane and tetraethoxysilane (TEOS); vinyltrimethoxysilane and tetramethoxysilane; vinyltriethoxysilane and methyltriethoxysilane; vinyltriethoxysilane, methyltriethoxysilane and tetraethoxysilane; vinyltrimethoxysilane and methyltrimethoxysilane; vinyltrimethoxysilane, methyltrimethoxysilane and tetraethoxysilane or tetramethoxysilane; vinyltriethoxysilane and ethyltriethoxysilane; vinyltriethoxysilane, ethyltriethoxysilane and tetraethoxysilane; vinyltrimethoxysilane and ethyltrimethoxysilane; vinyltrimethoxysilane, ethyltrimethoxysilane and tetraethoxysilane or tetramethoxysilane; vinyltriethoxysilane and propyltriethoxysilane; vinyltriethoxysilane, propyltriethoxysilane and tetraethoxysilane; vinyltrimethoxysilane and propyltrimethoxysilane; vinyltrimethoxysilane, propyltrimethoxysilane and tetraethoxysilane or tetramethoxysilane; vinyltriethoxysilane and isobutyltriethoxysilane; vinyltriethoxysilane, isobutyltriethoxysilane and tetraethoxysilane; vinyltrimethoxysilane and isobutyltrimethoxysilane; vinyltrimethoxysilane, isobutyltrimethoxysilane and tetramethoxysilane; vinyltrimethoxysilane and heptyltrimethoxysilane; vinyltrimethoxysilane and heptyltriethoxysilane; vinyltrimethoxysilane and hexyltrimethoxysilane; vinyltrimethoxysilane and hexyltriethoxysilane; vinyltriethoxysilane and octyltriethoxysilane; vinyltriethoxysilane, octyltriethoxysilane and tetraethoxysilane; more particularly with vinyltriethoxysilane and tetraethoxysilane in a ratio of 1:0.20 to 1:0; vinyltrimethoxysilane and octyltrimethoxysilane; vinyltrimethoxysilane, octyltrimethoxysilane and tetramethoxysilane; more particularly with vinyltrimethoxysilane and tetramethoxysilane in a ratio of 1:0.20 to 1:0; vinyltriethoxysilane and hexadecyltriethoxysilane; vinyltrimethoxysilane and hexadecyltrimethoxysilane; vinyltriethoxysilane and tetramethoxysilane in a ratio of 1:0.2 to 1:0, and hexadecyltriethoxysilane; vinyltrimethoxysilane and tetramethoxysilane in a ratio of 1:0.2 to 1:0 and hexadecyltrimethoxysilane.

Also used with particular preference in the process of the invention, in each case independently, are at least one cyclohexenyl-2-ethylene-trialkoxysilane, 3'-cyclohexenyl-2-ethylene-trialkoxysilane or cyclohexadienyl-C1 to C8-alkylene groups. Alternatively, likewise with particular preference, it is possible, as combinations in the process of the invention, in each case independently, for at least one cyclohexenyl-2-ethylene-trialkoxysilane, 3'-cyclohexenyl-2-ethylene-trialkoxysilane or cyclohexadienyl-C1 to C8-alkylene groups to be reacted with one of the aforementioned alkylalkoxysilanes.

Particularly preferred processes are based on the reaction of, or preferred siloxane oligomers are obtainable by the reaction of, a) vinyltriethoxysilane, b) vinyltrimethoxysilane, c) vinyltriethoxysilane and propyltriethoxysilane, vinyltrimethoxysilane and propyltrimethoxysilane, vinyltrimethoxysilane and propyltriethoxysilane, or vinyltriethoxysilane and propyltrimethoxysilane, or by reaction of a), b), c) in each case independently with tetraethoxysilane, or of a), b) and c) in each case independently with tetramethoxysilane.

Additionally or alternatively to one of the aforementioned features, it is also possible in the process to use, as processing assistant, at least one silicone oil, such as polydimethylsiloxane, paraffin, liquid paraffin, or a mixture comprising one of these processing assistants. One particularly preferred processing assistant is polydimethylsiloxane, preferably with a kinematic viscosity of around 150 to 400 mm$^2$/s, particularly preferred alternatives having a kinematic viscosity of around 200 mm$^2$/s or around 350 mm$^2$/s.

The invention also provides the following process for producing the composition, and also a composition obtainable by this process, especially featuring particularly low VOC, preferably with the following individual steps:

1) at least one olefinically functionalized alkoxysilane of the formula II, optionally an alkoxysilane of the formula III and/or an alkoxysilane of the formula IV, optionally as a mixture, are introduced preferably as an initial charge; optionally a solvent is added for dilution, preferably the corresponding alcohol to the hydrolysis alcohol.

2) At least one acidic hydrolysis and/or condensation catalyst, such as HCl, an organic saturated or unsaturated carboxylic acid, with a defined amount of water, is added. The pH set here is preferably less than 7, preferably from 1 to 6, more preferably from 3 to 5. Alternatively it is possible optionally to prepare a mixture (1+2) comprising at least one of the silanes of the formula II, III and/or IV, optionally with an alcohol in an amount by weight of 0.2 to 8 times in relation to the silanes (step (2a) of the formulae II, III and/or IV, more particularly methanol or ethanol, depending on the alkoxysilane used, and a defined amount of water (step (2a)); preferably at least one acidic hydrolysis and/or condensation catalyst, such as HCl, is in solution in the defined amount of water. The pH set here is preferably less than 7, preferably from 1 to 6, more preferably from 3 to 5.

Step (2a): The addition is made, preferably in an initial charge vessel, such as a stirred tank, with mixing, and, as a defined amount of water, greater than or equal to 1.0 to 1.6 mol of water, preferably 1.05 to 1.59, more preferably 1.1 to 1.58, very preferably greater than 1.2 to 1.57, more particularly 1.25 to 1.55 mol of water per mole of silicon atoms of the alkoxysilanes of the formula II and also optionally III and/or IV, and also all numerical values included within these boundaries, such as 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54. The defined amount of water may be metered in continuously or with at least one interruption over a period of 1 to 1000 minutes (29. I, cf. Claim 29). The temperature in the reaction mixture is set preferably at 5 to 90° C. for the reaction, preferably at 20 to 55° C., more preferably at 30 to 40° C. or at about 35° C. Following the addition of the mixture, the temperature of the reaction mixture formed is increased further, being set more particularly at the reflux temperature of the alcohol. For example, by heating of the reaction mixture to a temperature of 40 to 80° C., preferably of 50 to 80° C., more preferably of around 55 to 80° C., in accordance with the invention to about the boiling temperature of the alcohol. Over a period of at least 10 minutes to 36 hours, preferably 10 min to 8 h, at a reaction temperature of 5 to 80° C., preferably 40 to 80° C., the reaction mixture may continue reacting (29.ii, cf. Claim 29), preferably with mixing, for example with stirring, and 3) after the end of reaction, the alcohol is removed. Heating under reflux is carried out preferably for a number of hours, for example about 2 to 10 hours, preferably 3 to 5 hours, more preferably around 3.5 hours, and subsequently 4) the alcohol, comprising the hydrolysis alcohol and the alcohol employed, and also, optionally, water, are removed by distillation, preferably under reduced pressure and at elevated temperature, preferably until the reaction mixture or the resulting composition is substantially solvent-free, more particularly alcohol-free. The alcohol is distilled preferably at a liquid phase temperature of 0° C. to 100° C. under a pressure of 300 bar to 1 mbar, and at the same time HCl is distilled off, more preferably at 40° C. to 100° C. under a pressure of 250 bar to 10 bar.

5) Then it is possible to establish atmospheric pressure, and (30.i, cf. Claim 30) a defined amount of alcohol can be subsequently added and/or (step 30.ii) a defined amount of alkali metal, preferably sodium, alkaline earth metal, preferably magnesium or calcium, aluminium, metal hydride, preferably Li aluminium hydride, aluminium hydride, or a base can be added, more particularly gaseous ammonia, Li diisopropylamide, Li isopropylhexylamide, hexamethyldisilazane, alkali metal alkoxide, such as Na or K methoxide or Na or K ethoxide, alkali metal alkylate, such as butyl-Li adds. Optionally further distillation takes place under reduced pressure, and on addition of an alkali metal the mixture is left to react. The liquid-phase product can be filtered or decanted following the distillation. Alternatively or additionally it may be contacted with an ion exchanger, as described above. This gives the composition, in accordance with the invention, of olefinically functionalized siloxane oligomers, with a free alcohol content of less than (≤) 2 wt % and a chlorine content of ≤250 wt ppm, based on the composition having a viscosity of less than or equal to 1000 mPa s.

To the skilled person it is clear that the functional siloxane oligomers prepared in this way, depending on their desired application, may be diluted with a diluent or else may be admixed or compounded with a polymer, such as a thermoplastic base polymer, such as PE, PP or an elastomer, such as EVA. Further thermoplastic base polymers and elastomers are given as examples below; the skilled person is aware that in general all thermoplastic base polymers or polymers or elastomers are suitable. The skilled person knows of customary diluents for alkoxysilanes, examples that may be mentioned here being alcohols, ethers, ketones, hydrocarbons, or else mixtures of these. Depending on their desired application, therefore, the compositions of the functional siloxane oligomers may be prepared as a concentrate or else as a dilute composition from 99.9 to 0.001 wt %, and also all values situated in between, of functional siloxane oligomers in the overall composition. Preferred dilutions contain 10 to 90 wt % of functional siloxane oligomers, more preferably 20 to 80 wt %, with further preference 30 to 70 wt %.

Thermoplastic base polymers are understood in the sense of the invention to be, in particular, acrylonitrile-butadiene-styrene (ABS), polyamides (PA), polymethyl methacrylate (PMMA), polycarbonate (PC), polyethylene (PE), such as LDPE, LLDPE, mPE, polypropylene (PP), polystyrene (PS), polyvinyl chloride (PVC), chloroprene, and also the ethylene-unit-based polymers ethylene-vinyl acetate copolymers (EVA), EPDM or EPM, and/or celluloid or silane-co-polymerized polymers, and base polymers prepared, for example, from unsaturated functional monomers including silanes, such as VTMO, VTEO, and monomers such as ethylene and other olefins, and also monomers and/or prepolymers precursor compounds of these base polymers, such as ethylene, propylene. Further preferred elastomers may be selected from the series of ethylene-propylene rubber (EPR), ethylene-propylene-diene rubber (EPDM), styrene-butadiene rubber (SBR), natural rubber (NR), acrylate copolymer rubber (ACM), acrylonitrile-butadiene rubber (NBR) and/or polybutadiene rubber (BR).

Also provided by the invention is a composition obtainable from the reaction of an olefinic alkoxysilane of the formula II, optionally with at least one alkoxysilane of the formula III and/or formula IV, in the presence of a defined amount of water of greater than or equal to 1.1 to 1.59 mol of water per mole of silicon atoms in the alkoxysilanes used, and preferably a solvent, such as an alcohol, more particularly comprising olefinically functionalized siloxane oligomers in which the amount of silicon atoms with a T structure is greater than 10%, more particularly greater than or equal to 11%, and in which the total chloride content of these compositions is at the same time advantageously less than 250 mg/kg, more particularly less than 80 mg/kg, with further preference less than 50 mg/kg, in relation to the overall composition. The compositions thus obtainable may be diluted at any time simply with a diluent.

In order to permit rapid distribution in the extruder, without suffering excessive mass losses in the hot extruders, a balanced ratio between the molecular weight Mw and the TGA temperature at which 5% or 50% mass loss occurs should be maintained. The abovementioned compounds customarily exhibit mass loss of 50% at temperatures well above 200° C., more particularly above 220° C. The compositions of the invention are therefore very suitable for application in extruders, and at the same time, by virtue of the very narrowly set molecular weight, permit rapid distribution of the siloxane oligomers in the thermoplastics. Also conducive to this effective distribution are the slightly increased T structures in the siloxanes, since the molecules are more compact.

Also provided by the invention is the use of the composition of the invention or of the compositions produced by the process of the invention as adherence agent, as crosslinking agent by graft polymerization and/or hydrolytic condensation in a conventional way, for producing polymers grafted with olefinically functionalized siloxane oligomers, prepolymers and/or mineral-filled polymers (compounds), for producing polymers grafted with olefinically functionalized siloxane oligomers, prepolymers and/or mineral-filled thermoplastics or elastomers, preferably mineral-filled thermoplastics, elastomers or prepolymers thereof, for the grafting or in the polymerization of thermoplastic polyolefins, as drying agent, more particularly as water scavenger for silicone sealants, in crosslinkable polymers for producing cables, for producing crosslinkable polymers, as oil phase in an emulsion and/or together with organosilanes or organopolysiloxanes, for filler modification (filler coating), resin modification, resin additive, surface modification, surface functionalization, surface hydrophobization, as constituent in coating systems, as constituent in sol-gel systems or hybrid systems, hybrid coating systems, for modifying cathodes and anode materials in batteries, as electrolyte fluid, as additive in electrolyte fluids, for modifying fibres, more particularly glass fibres and natural fibres, and for modifying textiles, for modifying fillers for the artificial stone industry, as architectural preservative or constituent in architectural preservative, as additive for mineral-hardening compositions, for modifying wood, wood fibres and cellulose. With regard to the joint use, according to the invention, of the composition with organosilanes or organosiloxanes, reference is made in full to the disclosure content of EP 1 205 481 B1, more particularly to the disclosure content of paragraph [0039] and to the list of organosilanes and organosiloxanes that is disclosed therein. Furthermore, the entire disclosure content of DE 10 2011 086 863.1 with the filing date of 22 Nov. 2011, filed at the German Patent and Trade Mark Office, is made part of the content of the present invention.

The invention is elucidated in more detail by the examples below, without being confined to these working examples.

EXAMPLES

Determination of molecular weight: Molar masses and also the molar mass distribution can be determined by means of gel permeation chromatography (GPC). The GPC analysis technique is described comprehensively in publications including "Modern Size-Exclusion Liquid Chromatography", Andre Striegel et al., Verlag Wiley & Sons, 2nd edn. 2009. To calibrate the method for siloxane analyses it is possible here to use, for example, divinyltetramethoxydisiloxane or divinyltetraethoxydisiloxane as a standard. Percentages in relation to the olefinic siloxane oligomers in the present document correspond to a datum in area per cent, which can be determined from GPC analyses. MZ-Analysetechnik columns used: columns: 50×8.0 mm, MZ-Gel SDplus (styrene/divinylbenzene copolymer with high degree of crosslinking, spherical particle shape), porosity 50 Å (angstroms, Å), 5 µm (micrometres) (preliminary column), 300× 8.0 mm, MZ-Gel SDplus, porosity 50 Å (angstroms, Å), 5 µm, 300×8.0 mm, MZ-Gelplus, porosity 100 Å (angstroms, Å), 5 µm, 300×8.0 mm, MZ-Gel SDplus, porosity 500 Å (angstroms, Å), 5 µm; eluent and pump flow: methyl ketone (MEK) at 1 ml/min, standard substance: internal standard—1 g/l ethylbenzene in 1% strength sample solution. The measuring instrument is calibrated beforehand against the respective substance (monomer, dimer, trisiloxane, etc.). Measuring instruments from Agilent: 1100 Series isotactic pump G1310A, 1100 Series column oven G1316A, 1100 Series RID detector G1362A, manual injector G1328A, vacuum degasser G1322A, GPC software (PSS WinGPC Unity).

Determination of Total Chloride: In a bomb calorimeter, the silane is digested with oxygen and then hydrolysed with acetic acid and hydrofluoric acid. The chloride content of the resulting solution is ascertained by titration with silver nitrate.

Determination of Hydrolysable Chloride: Following hydrolysis with acetic acid, the chloride content is determined by titration with silver nitrate.

Determination of $SiO_2$ Content: Crucible Method: The $SiO_2$ content is determined by acid digestion with concentrated sulphuric acid and subsequent evaporation, by fluorination.

GC Analysis: Standard GC assay method, in which the monomer content is determined by suitable calibration and possibly internal standard.

Alcohol after Hydrolysis: A defined amount of a sample is admixed with sulphuric acid (25% strength). Then a defined amount of water is added and neutralization takes place with aqueous sodium hydroxide solution (20% strength). After a steam distillation has been carried out, the alcohol content is determined by GC against an internal standard (sec-butanol, HP 5890 with HP 3396 integrator, 1 ml/min).

Flash Point Determination: DIN EN ISO 13736 (January 2009), DIN EN ISO 2719 (September 2003). Flash points above 40° C. are determined by means of DIN EN ISO 2719 (=DIN 51758=EN 22719), and between −30° C. and +40° C. according to DIN EN ISO 13736 (=DIN 51755).

Water Content: Karl-Fischer (DIN 51777)

TGA: In the TGA (thermogravimetric analysis), a sample for analysis is placed, in a crucible, onto a balance. The sample itself is located, during the measurement, in a heatable oven. The crucible is usually open (no lid, or lid with holes). The interior of the oven is flushed with an inert gas (N2) in order to prevent possible reactions resulting from oxygen contact.

Instrument: TG 209 from Netzsch, temperature range: RT to about 1000° C. Heating rate: 10 K/min, initial mass: about 10-12 mg, crucible: platinum with hole in the lid.

Further information on TGA analyses is found in, for example, the following Internet textbook: Moderne Pharmazeutische Technologie 2009, Cornelia M. Keck, Reiner H. Müller, Section 3.5, Thermoanalysis, Lothar Schwabe, FU Berlin, page 76, Fig.: 5, http://pharmazie-lehrbuch.de/Moderne %20Pharmazeutische %20 Technologie.pdf or in other textbooks on analytical methods.

$^{29}$Si NMR Spectrometry: Furthermore, the monomer content, and also M, D and T structures, can be determined using $^{29}$Si NMR spectrometry, which is likewise well known to the skilled person.

Determination of Dynamic Viscosity: The dynamic viscosity was determined in accordance with DIN 53015.

1. Syntheses of Inventive Products

The respective methods for reducing the chlorine content may, as elucidated above, each be combined, independently of one another, with the present technique as well. For example, the use of a well-defined amount of water may be combined with the use of the ion exchanger and/or with the addition of a second to sixth defined amount of alcohol subsequent to the reaction and/or with neutralization by means of a base and/or with the addition of a reducing agent.

1.1 "VTEO-siloxane oligomer"—silane:water=1:1.1—V092

Procedure: A 2 l apparatus is charged with 380.6 g of VTEO (vinyltriethoxysilane).

Then a mixture of ethanol, double-distilled water and hydrochloric acid (37%) is metered in at 35° C. under ambient pressure. There is an exothermic reaction. Should the temperature rise above 60° C., metering is interrupted. The total reaction time runs to 5 hours of stirring, beginning at 77° C., after complete addition of the $H_2O$/EtOH/HCl mixture. After the reaction, the alcohol is distilled on a rotary evaporator at up to 100° C. and 100 mbar. When 100 mbar has been reached, it is maintained for 15 minutes, after which the system is let down. The liquid phase obtained is a VTEO-siloxane oligomer.

TABLE 1

| Raw materials V092 | |
|---|---|
| Compound | Initial mass |
| Water | 39.6 g |
| Ethanol | 181.2 g |
| Hydrochloric acid (37% strength) | 0.24 g |

1.2 "VTEO-Siloxane Oligomer"—Silane:Water=1:1.22—V093

Procedure: A 2 l apparatus is charged with 380.6 g of VTEO. Then a mixture of ethanol, double-distilled water and hydrochloric acid (37%) is metered in at 35° C. under ambient pressure. There is an exothermic reaction. Should the temperature rise above 60° C., metering is interrupted. The total reaction time runs to 5 hours of stirring, beginning at 77° C., after complete addition of the $H_2O$/EtOH/HCl mixture. After the reaction, the alcohol is distilled on a rotary evaporator at up to 100° C. and 100 mbar. When 100 mbar has been reached, it is maintained for 15 minutes, after which the system is let down. The liquid phase obtained is vinylsiloxane oligomer.

TABLE 2

| Raw materials V093 | |
|---|---|
| Compound | Initial mass |
| Water | 43.9 g |
| Ethanol | 181.0 g |
| Hydrochloric acid (37% strength) | 0.26 g |

1.3 "VTEO-Siloxane Oligomer"—Silane:Water=1:1.35—V094

Procedure: A 2 l apparatus is charged with 380.6 g of VTEO. Then a mixture of ethanol, double-distilled water and hydrochloric acid (37%) is metered in at 35° C. under ambient pressure. There is an exothermic reaction. Should the temperature rise above 60° C., metering is interrupted. The total reaction time runs to 5 hours of stirring, beginning at 77° C., after complete addition of the H₂O/EtOH/HCl mixture. After the reaction, the alcohol is distilled on a rotary evaporator at up to 100° C. and 100 mbar. When 100 mbar has been reached, it is maintained for 15 minutes, after which the system is let down. The liquid phase obtained is vinylsiloxane oligomer.

TABLE 3

| Raw materials V094 | |
|---|---|
| Compound | Initial mass |
| Water | 49.0 g |
| Ethanol | 181.2 g |
| Hydrochloric acid (37% strength) | 0.23 g |

1.4 "VTEO-siloxane oligomer"—silane:water=1:1.47—V095

Procedure: A 2 l apparatus is charged with 380.6 g of VTEO. Then a mixture of ethanol, double-distilled water and hydrochloric acid (37%) is metered in at 35° C. under ambient pressure. There is an exothermic reaction. Should the temperature rise above 60° C., metering is interrupted. The total reaction time runs to 5 hours of stirring, beginning at 77° C., after complete addition of the H₂O/EtOH/HCl mixture. After the reaction, the alcohol is distilled on a rotary evaporator at up to 100° C. and 100 mbar. When 100 mbar has been reached, it is maintained for 15 minutes, after which the system is let down. The liquid phase obtained is vinylsiloxane oligomer.

TABLE 4

| Raw materials V095 | |
|---|---|
| Compound | Initial mass |
| Water | 53.3 g |
| Ethanol | 181.0 g |
| Hydrochloric acid (37% strength) | 0.27 g |

1.5 "VTEO/TEOS-Silane Oligomer"—Silane:Water=(1+0.1):1.22—V096

Procedure: A 2 l apparatus is charged with 380.6 g of VTEO and 41.6 g of tetraethoxysilane (TEOS). Then a mixture of ethanol, double-distilled water and hydrochloric acid (37%) is metered in at 35° C. under ambient pressure. There is an exothermic reaction. Should the temperature rise above 60° C., metering is interrupted. The total reaction time runs to 5 hours of stirring, beginning at 77° C., after complete addition of the H₂O/EtOH/HCl mixture. After the reaction, the alcohol is distilled on a rotary evaporator at up to 100° C. and 100 mbar. When 100 mbar has been reached, it is maintained for 15 minutes, after which the system is let down. The liquid phase obtained is a vinyl-functionalized cooligomer with co-condensed Q structural elements derived from tetraethoxysilane (VTEO/TEOS-siloxane oligomer).

TABLE 5

| Raw materials V096 | |
|---|---|
| Compound | Initial mass |
| Water | 44.2 g |
| Ethanol | 181.6 g |
| Hydrochloric acid (37% strength) | 0.23 g |

1.6 "VTEO/PTEO-Siloxane Oligomer"—Silane:Water=1:1.25—V111

Procedure: A 2 l four-necked apparatus with water cooling and magnetic stirrer is charged with 190.3 g of VTEO and 206.5 g of PTEO. Then a mixture of ethanol, double-distilled water and hydrochloric acid (37%) is metered in at 35° C. under ambient pressure. There is an exothermic reaction. Should the temperature rise above 60° C., metering is interrupted. The total reaction time runs to 5 hours, beginning at 79° C., after complete addition of the H₂O/EtOH/HCl mixture. After the reaction, the alcohol is distilled on a rotary evaporator at up to 100° C. and 100 mbar. When 100 mbar has been reached, it is maintained for 15 minutes, after which the system is let down. The liquid phase obtained is a vinyl- and propyl-functionalized siloxane oligomer from VTEO and PTEO.

TABLE 6

| Raw materials V111 | |
|---|---|
| Compound | Initial mass |
| Water | 45.2 g |
| Ethanol | 175.0 g |
| Hydrochloric acid | 0.2 g |

1.7 "VTEO/PTEO-Siloxane Oligomer"—Silane:Water=1:1.5—V112

Procedure: A 2 l four-necked apparatus with water cooling and magnetic stirrer is charged with 190.3 g of VTEO and 206.6 g of PTEO. Then a mixture of ethanol, double-distilled water and hydrochloric acid (37%) is metered in at 35° C. under ambient pressure. There is an exothermic reaction. Should the temperature rise above 60° C., metering is interrupted. The total reaction time runs to 5 hours, beginning at 79° C., after complete addition of the H₂O/EtOH/HCl mixture. After the reaction, the alcohol is distilled on a rotary evaporator at up to 100° C. and 100 mbar. When 100 mbar has been reached, it is maintained for 15 minutes, after which the system is let down. The liquid phase obtained is a vinyl- and propyl-functionalized siloxane oligomer from VTEO and PTEO.

TABLE 7

| Raw materials V112 | |
|---|---|
| Compound | Initial mass |
| Water | 54.3 g |
| Ethanol | 175.0 g |
| Hydrochloric acid | 0.2 g |

1.8 "Vteo/Pteo/Teos-Siloxane Oligomer"—Silane:Water=(1+0.1):1.25—V113

Procedure: A 2 l four-necked apparatus with water cooling and magnetic stirrer is charged with 190.3 g of VTEO, 41.5 g of tetraethoxysilane and 206.4 g of PTEO. Then a mixture of ethanol, double-distilled water and hydrochloric acid (37%) is metered in at 35° C. under ambient pressure. There is an exothermic reaction. Should the temperature rise above 60° C., metering is interrupted. The total reaction time runs to 5 hours, beginning at 79° C., after complete addition of the H$_2$O/EtOH/HCl mixture. After the reaction, the alcohol is distilled on a rotary evaporator at up to 100° C. and 100 mbar. When 100 mbar has been reached, it is maintained for 15 minutes, after which the system is let down. The liquid phase obtained is a crosslinked, vinyl- and propyl-functionalized siloxane oligomer with Q structural elements (quator functionality) from VTEO, PTEO and tetraethoxysilane.

TABLE 8

Raw materials V113

| Compound | Initial mass |
| --- | --- |
| Water | 45.2 g |
| Ethanol | 174.8 g |
| Hydrochloric acid | 0.19 g |

2. Analysis
2.1 General Analysis

TABLE 9

Analytical results for the siloxane oligomers of VTEO type

|  | V092 | V093 | V094 | V095 | V096 |
| --- | --- | --- | --- | --- | --- |
| Total chloride [mg/kg] | <35 | <35 | <35 | 50 | <35 |
| hydrol. chloride [mg/kg] | <3 | 4 | 4 | 6 | 5 |
| SiO$_2$ [% (mass)] | 50.8 | 53.6 | 55.8 | 58.7 | 52.2 |
| free ethanol [% (mass)] | 1.5 | 1.4 | 1.5 | 1.4 | 0.7 |
| VTEO [% (mass)] | 0.5 | 0.2 | <0.1 | <0.1 | 0.3 |
| Colour number [mg Pt Co/l] | <5 | <5 | 10 | <5 | 10 |
| Density at 20° C. [g/cm$^3$] | 1.061 | 1.088 | 1.108 | 1.123 | 1.082 |
| dyn. viscosity at 20° C. [mPa s] | 7.8 | 13.8 | 22.9 | 46.6 | 11.5 |

TABLE 10

Analytical results of the VTEO/PTEO siloxane oligomers

|  | V111 | V112 | V113 |
| --- | --- | --- | --- |
| Total chloride [mg/kg] | 55 | 65 | 110 |
| hydrol. chloride [mg/kg] | <3 | 4 | 4 |
| SiO$_2$ [% (mass)] | 50.1 | 54.5 | 47.8 |
| free ethanol [% (mass)] | 0.9 | 1.2 | 0.8 |
| VTEO/PTEO (% (mass)) | 0.1 | 0.1 | 0.4 |
| Colour number [mg Pt Co/l] | <5 | <5 | <5 |
| Density at 20° C. [g/cm$^3$] | 1.053 | 1.087 | 1.044 |
| dyn. viscosity at 20° C. [mPa · s] | 17.8 | 48.1 | 11.5 |

2.2 NMR Analyses

TABLE 11

Results from the NMR studies of the siloxane oligomers of VTEO, VTEO/PTEO and VTEO/PTEO/TEOS types

| Experiment No. | $^1$H and $^{13}$C NMR analytical results | $^{29}$Si NMR analytical results - Fractions in the siloxane oligomer compositions | | | |
| --- | --- | --- | --- | --- | --- |
|  |  | Silane monomer [mol %] | M structure [mol %] | D structure [mol %] | T structure [mol %] |
| V092 | 1.02 mol SiOEt and 0.03 mol EtOH | 0.3 (VTEO) | 30.2 (VS) | 58.0 (VS) | 11.5 (VS) |
| V093 | 0.83 mol SiOEt and 0.03 mol EtOH | — | 18.0 (VS) | 63.3 (VS) | 18.7 (VS) |
| V094 | 0.67 mol SiOEt and 0.04 mol EtOH | — | 12.9 (VS) | 64.3 (VS) | 22.8 (VS) |
| V095 | 0.55 mol SiOEt and 0.03 mol EtOH | — | 6.8 (VS) | 63.0 (VS) | 30.2 (VS) |
| V096 | 1.1 mol SiOEt | 0.2 (VTEO) | 20.8 (VS) | 55.6 (VS) | 14.0 (VS) |
|  |  | — | 1.7 (ES) | 5.6 (ES) | 2.3 (ES) |
| V111 | 1.0 mol propylsilyl 1.7 mol SiOEt | 0.1 (PTEO) | 4.8 (VS) 16.7 (PS) | 33.1 (VS) 28.7 (PS) | 6.6 (VS) (superimposed) |
| V112 | 1.0 mol propylsilyl 1.2 mol SiOEt | — | 10.6 (VS) 7.8 (PS) | 33.7 (VS) 34.2 (PS) | 13.7 (VS) (superimposed) |
|  |  | — | 21.8 (PS) | 21.9 (PS) | 1.5 (PS) |
|  |  | — | 2.3 (ES) | 6.1 (ES) | 1.2 (ES) |

[VS = vinylsilyl, PS = propylsilyl, ES = ethoxysilyl]

2.3 GPC Analyses

TABLE 12a

Evaluation of the GPC analysis results

| Experiment No. | Mn [g/mol] | Mw [g/mol] | D = $M_w/M_n$ |
|---|---|---|---|
| V092 | 495.24 | 564.87 | 1.1406 |
| V093 | 538.55 | 621.30 | 1.1536 |
| V094 | 576.26 | 679.77 | 1.1796 |
| V095 | 624.38 | 754.87 | 1.2090 |
| V096 | 550.08 | 710.87 | 1.2923 |
| V111 | 581.50 | 816.27 | 1.4037 |
| V112 | 763.06 | 1083.40 | 1.4198 |
| V113 | 556.68 | 707.65 | 1.2735 |
| V078 | 275.13 | 291.11 | 1.0581 |
| V081 | 254.06 | 269.90 | 1.0624 |

TABLE 12b

Evaluation of the GPC analysis results of the compositions prepared in analogy to Example 1.1 (V092), Example 1.2 (V093), Example 1.3 (V094) and in analogy to Example 1.4 (V095)

| analogous | Mw g/mol | Mn g/mol | Mmax [g/mol] |
|---|---|---|---|
| V092 | 567.4 | 504.8 | 1800 |
| V093 | 624.3 | 551.2 | 2000 |
| V094 | 685.3 | 601.3 | 2100 |
| V095 | 783.5 | 643.7 | 3000 |

TABLE 12c

Evaluation of the GPC analysis results, fractions in area % of the compositions prepared in analogy to Example 1.1 (V092), Example 1.2 (V093), Example 1.3 (V094) and in analogy to Example 1.4 (V095), to 100% less than disiloxane and greater than hexasiloxane, where less than disiloxane is less than 1.0%, more particularly less than 0.5%.

| analogous | Disiloxane + cyclotrisiloxane [%] | Trisiloxane + cyclotetrasiloxane [%] | Tetrasiloxane + cyclopentasiloxane [%] | Pentasiloxane + cyclohexasiloxane [%] |
|---|---|---|---|---|
| V092 | 11.6 | 35.8 | 26.1 | 10.2 |
| V093 | 6 | 30.2 | 31.2 | 9.9 |
| V094 | 3.6 | 26 | 31.1 | 10.1 |
| V095 | 1.2 | 21.9 | 31 | 8.6 |
| V096 | 6.3 | 27.3 | 28.8 | 10.4 |

TABLE 12d

Evaluation of the GPC analysis results, fractions in area % of the compositions prepared in analogy to Example 1.1 (V092), Example 1.2 (V093), Example 1.3 (V094) and in analogy to Example 1.4 (V095), to 100% less than 250 g/mol and greater than 1000 g/mol, where less than 250 g/mol is less than 1.0%, more particularly less than 0.5%.

| analogous | 250-500 rel. MW [%] | 500-750 rel. MW [%] | 750-1000 rel. MW [%] |
|---|---|---|---|
| V092 | 46.63 | 36.85 | 11.48 |
| V093 | 35.54 | 41.7 | 14.23 |
| V094 | 28 | 42.21 | 16.34 |
| V095 | 21.84 | 40.42 | 17.38 |
| V096 | 32.55 | 39.41 | 15.11 |

The deviations in the molecular weight for individual compositions of siloxane oligomers are explained on the one hand by the different substitution of the siloxane oligomers or, in the case of identical substitution, by customary, minor fluctuations within the individual experiments.

2.4 TGA

TABLE 13a

Evaluation of the TGA analysis results
Siloxane oligomers

| Experiment number | V092 | V093 | V094 | V095 | V096 |
|---|---|---|---|---|---|
| 5% mass loss at T = | 170° C. | 185° C. | 197° C. | 211° C. | 174° C. |
| 50% mass loss at T = | 252° C. | 291° C. | 530° C. | — | 267° C. |
| Mass loss [%] at 150° C. | 3% | 1% | 1% | 0% | 2% |
| Mass loss [%] at 200° C. | 15% | 8% | 6% | 3% | 12% |

TABLE 13b

Evaluation of the TGA analysis results
Siloxane oligomers

| Experiment number | V111 | V112 | V113 |
|---|---|---|---|
| 5% mass loss at T = | 189° C. | 206° C. | 177° C. |
| 50% mass loss at T = | 286° C. | 491° C. | 256° C. |
| Mass loss [%] at 150° C. | 1% | 1% | 1% |
| Mass loss [%] at 200° C. | 8% | 4% | 13% |

3. Comparative examples

Comparative Example 1

V078—Example 1 from EP 0 518 057
B1—Preparation of a Co-Condensate of Vinyltrimethoxysilane and Methyltrimethoxysilane with a Molar Vinyl:Methoxy Groups Ratio of Around 1:3

Procedure: A 2 l four-necked apparatus with water-operated condenser and magnetic stirrer was charged with 397.6 g of vinyltrimethoxysilane (VTMO) and 244.6 g of methyltrimethoxysilane at 20° C. The mixture was admixed, using a 500 ml dropping funnel, with a solution of 49.9 g of distilled water in 332.8 g of methanol, this solution containing 2400 ppm of hydrogen chloride. After a total of 16 hours, the entire methanol together with HCl was distilled off at about 300 mbar. Thereafter the resulting oligomer mixture was distilled to a pressure of about 1 mbar and a boiling range ending at 113° C. In this way, 170 g of clear product were obtained.

TABLE 14

Raw materials V078

| Compound | Supplier | Initial mass |
|---|---|---|
| VTMO | Evonik Degussa GmbH | 397.6 g |
| MTMS | Evonik Degussa GmbH | 244.6 g |
| Hydrochloric acid 2400 ppm | Merck (HCl 37%) Double-distilled water | 49.9 g |
| Methanol | ROTH | 332.8 g |

Comparative Example 2

V081—Example 6 from EP 0518057 B1—Preparation of a Condensate of Vinyltrimethoxysilane with a Molar Vinyl:Methoxy Groups Ratio of about 1:1.75

Procedure: A 2 l four-necked apparatus with water-operated condenser and magnetic stirrer was charged with 693.83 g of VTMO at 20° C. The mixture was admixed with a solution of 52.82 g of distilled water in 351.53 g of methanol, the solution containing 1100 ppm of hydrogen chloride. A 500 ml dropping funnel was used for this purpose. The temperature rose to about 36° C. within 26 minutes. After a total of 13 hours, the entire methanol together with hydrochloric acid was distilled off over 2-3 hours at approximately 300 mbar. The resulting oligomer mixture was thereafter distilled down to a pressure of about 1 mbar and a boiling range ending at 100° C. In this way, 240 g of clear product were obtained.

TABLE 15

Raw materials V081

| Compound | Supplier | Initial mass |
|---|---|---|
| VTMO | Evonik Degussa GmbH | 693.7 g |
| Methanol | | 351.5 g |
| Hydrochloric acid 1100 ppm | Merck (HCl 37%) Double-distilled water | 52.8 g |

The chloride content (total chloride) can be determined by the methods known to the skilled person, such as potentiometric determination with $AgNO_3$. The hydrolysable chloride is titrated potentiographically with $AgNO_3$.

TABLE 16

Analytical results for V078 (Comparative Example 1),

| Experiment No. V078 | Total chlorides [mg/kg] | hydrolysable chloride [mg/kg] | $SiO_2$ (mass) [%] | VTMO (mass) [%] | Colour number [mg Pt—Co/l] |
|---|---|---|---|---|---|
| Distillate (1) | 230 | 16 | 52.4 | <0.1 | <5 |

(1) (cf. Example 1 in EP0518057B1)

TABLE 17

Analytical results for V081 (Comparative Example 2),

| Experiment No. V081 | Total chloride [mg/kg] | Hydrolysable chloride [mg/kg] | $SiO_2$ (mass) [%] | VTMO (mass) [%] | Colour number [mg Pt—Co/l] |
|---|---|---|---|---|---|
| Distillate (2) | 50 | <3 | 48.6 | 1.7 | <5 |

(2) cf. Example 6 in EP0518057B1)

TABLE 18

Results from the $^{29}Si$ NMR analyses of the products from Comparative Experiments V078 and V081

| Comparative Experiment No. | Fractions in the siloxane oligomer compositions | | | |
|---|---|---|---|---|
| | M structure [mol %] | D structure [mol %] | T structure [mol %] | Silane monomer [mol %] |
| V078 | 52.1 (VS) 29.3 (MS) | 9.1 (VS) 8.6 (MS) | — (VS) — (MS) | 0.9 (VTMO) — (MTMS) |
| V081 | 91.8 (VS) | 6.8 (VS) | — (VS) | 1.2 (VTMO) |

[VS = vinylsilyl, MS = methylsilyl]

Comparative Examples 3 to 5 in Analogy to Example 6

EP 0518057

The procedure disclosed in Example 6 was reproduced in each case for the compound VTMO and carried out for the compounds VTEO and VTMO, and also for the cooligomers VTMO and propyltrimethoxysilane (PTMO) and for vinyltriethoxysilane (VTEO) with propyltriethoxysilane (PTEO), as new variants. The processes here were carried out with equimolar amounts in a 1000 g-scale batch size. A 2 l stirred apparatus was charged with each of the silanes at room temperature (vinyltrimethoxysilane (V074), vinyltriethoxysilane (V075), vinyltrimethoxy- and propyltrimethoxysilane (V076), and vinyltriethoxy- and propyltriethoxysilane (V077). The water/alcohol mixture (Examples V074, V076, methanol; Examples V075, V077=ethanol), containing 1100 ppm (0.11%) of hydrogen chloride in each case, was metered in. In each case an exothermic temperature profile was observed. The temperature here rose in each case to 35-40° C. After a reaction time of 13 hours, the alcohol was stripped off over 3 hours at an absolute pressure of 300 mbar. Finally the oligomer mixture itself was distilled off under a pressure <0.1 mbar.

TABLE 19

Analytical results - Comparative Examples 3 to 5 and new variant

| Experiment number | V074 | V075 | V076 | V077 |
|---|---|---|---|---|
| Remarks: Distillates | Example 6 | VTEO new variant Example 6 EP 0518057 | VTMO/PTMO new variant of Example 6, EP 0518057 | VTEO/PTEO new variant of Example 6 EP 0518057 |
| Silane A | VTMO 631.50 g | VTEO 614.46 g | VTMO 307.01 g | VTEO 301.35 g |
| Silane B | | | PTMO 340.35 g | PTEO 326.74 g |
| Catalyst (20% strength HCl) | 2.02 g | 2.12 g | 1.86 g | 2.04 g |
| Alcohol | 320.02 g | 348.69 g | 305.24 g | 335.55 g |
| Water | 46.46 g | 34.74 g | 45.53 g | 34.32 g |
| Yield (%), via mol Si | 37.40 | 93.75 | 76.02 | 89.62 |

TABLE 20

Analytical results for Comparative Examples 3 to 5,

| Experiment | V081 | V074 | V075 | V076 | V077 |
|---|---|---|---|---|---|
| Viscosity 20° C. [mPa · s] | | 2.1 | 2.3 | 3 | 2.6 |
| TGA | | | | | |
| Weight decrease % | | 99.5%, n.r. | 98.3%, (1.1) | 99.5%, (1.2) | 98.2% (1.3) |
| DTG 1(2) | | 176° C. and 196° C. | 196° C. | 222° C. | 209° C. |
| 5% mass loss at T = | 111° C. | 118° C. | 135° C. | 135° C. | 131° C. |
| 50% mass loss at T = | 164° C. | 162° C. | 197° C. | 203° C. | 202° C. |
| 95% mass loss at T = | | 209° C. | 235° C. | 243° C. | 238° C. |
| Mass loss [%] at 150° C. | 28 | 23 | 12 | 26 | 11 |
| Mass loss [%] at 200° C. | 99 | 86 | 59 | 49 | 50 | n.r.: no residue,
(1.1): individual black dots on crucible base;
(1.2) no residue apparent,
(1.3) black dots on crucible base and crucible base rim,
(2): Temperature at max. mass decrease rate [dm/dt] – first peak

TABLE 21

TGA evaluation

| | Examples | |
|---|---|---|
| | VTMO/MTMS | VTMO |
| Experiment number | V078 | V081 |
| 5% mass loss at T = | 114° C. | 111° C. |
| 50% mass loss at T = | 170° C. | 164° C. |
| Mass loss [%] at 150° C. | 23% | 28% |
| Mass loss [%] at 200° C. | 95% | 99% |

4. Performance Tests

TABLE 22

Assignment of the performance experiments

| Experiment No. (siloxane oligomer from) | PF experiment No. |
|---|---|
| — | V153 (blank sample) |
| V092 | V119 |
| V093 | V120 |
| V094 | V121 |
| V095 | V122 |
| V096 | V123 |
| V111 | V124 |
| V112 | V125 |
| V113 | V126 |
| V078 | V116 |
| V081 | V118 |

4.1 Kneading Experiments

The following kneading operations were carried out in a HAAKE kneading apparatus at a rotary speed of 30 rpm with a temperature profile of 3 min at 140° C., from 140° C. to 170° C. in 2 min, 5 min at 170° C. Subsequently, each batch was processed by compression to form two plates at 190° C. under a load pressure of 20 t. To simplify the addition of the peroxide, silane/peroxide solutions were prepared.

4.2 Preparation of the Measurement Specimens

The samples prepared were stored in a conditioning chamber at 23° C. and 50% relative atmospheric humidity, after which specimens were made for tensile tests and for the determination of the water uptake capacity and determination of the melt index.

TABLE 23

Raw materials and batches for practical application

| Compound | Batch |
|---|---|
| ATH | M56/15 |
| EVA | M56/156 |
| DCUP | M56/026 |

TABLE 24

Peroxide mixtures for kneadings

| Siloxane oligomer-DCUP solution from batch | Initial mass DCUP | Initial mass Siloxane oligomer | for experiment No. |
|---|---|---|---|
| V078 | 9.81 g | 0.19 g | V116 |
| V081 | 9.81 g | 0.19 g | V118 |
| V092 | 9.81 g | 0.19 g | V119 |
| V093 | 9.81 g | 0.19 g | V120 |
| V094 | 9.81 g | 0.19 g | V121 |
| V095 | 9.81 g | 0.19 g | V122 |

TABLE 24-continued

Peroxide mixtures for kneadings

| Siloxane oligomer-<br>DCUP solution<br>from batch | Initial mass<br>DCUP | Initial mass<br>Siloxane oligomer | for experiment<br>No. |
|---|---|---|---|
| V096 | 9.81 g | 0.19 g | V123 |
| V111 | 9.82 g | 0.19 g | V124 |
| V112 | 9.82 g | 0.19 g | V125 |
| V113 | 9.81 g | 0.19 g | V126 |

TABLE 25

Initial masses in the kneading experiments

| Experiment<br>No. | Initial<br>mass EVA | Initial<br>mass ATH | Initial mass<br>DCUP-siloxane<br>oligomer<br>solution | Siloxane<br>oligomer-DCUP<br>solution from<br>batch |
|---|---|---|---|---|
| V116 | 27.72 g | 41.61 g | 0.45 g | V078 |
| V118 |  |  | 0.44 g | V081 |
| V119 | 27.72 g | 41.61 g | 0.42 g | V092 |
| V120 |  |  | 0.44 g | V093 |
| V121 |  |  | 0.43 g | V094 |
| V122 |  |  | 0.43 g | V095 |
| V123 |  |  | 0.41 g | V096 |
| V124 | 27.72 g | 41.61 g | 0.42 g | V111 |
| V125 |  |  | 0.41 g | V112 |
| V126 |  |  | 0.42 g | V113 |
| V153 | 27.72 g | 41.61 g | — | — |

4.3 Determinations of the Melt Index (MFR) and of the Volume Flow Index (MVR)

Preparation and evaluation took place in accordance with DIN ISO 1133 (Method B), the content of which is referenced in full and made part of the content of the present application. Testing apparatus: Zwick 4106 flow tester. The determination of melt index (MRF) and volume flow index (MVR) is carried out under a fixed shearing load and at a defined temperature ($T_{PT}$) and defined loading ($m_{nom}$) on a polymeric melt through a standard nozzle. The change in travel of the die over time is ascertained, and MVR and MRF are calculated according to the formulae known to the skilled person. ~7 g of the individual samples were comminuted, and the melt index ("MFR") was determined at a temperature of 160° C. at a loading of 21.6 kg.

TABLE 26

MFR and MVR results for the comparative examples

| Experiment No. | V116 | V118 |
|---|---|---|
| Siloxane oligomer from | V078 | V081 |
| Experimental temperature | 160° C. | |
| Preheating time | 4 min | |
| Loading weight | 21.6 kg | |
| MFR [g min] | 3.19 | 3.39 |
| MVR [cm³ min] | 2.36 | 2.51 |
| Density [g/cm³] | 1.352 | 1.348 |

TABLE 27

MFR and MVR results for the blank sample

| Experiment No. | V153 (blank sample) |
|---|---|
| Siloxane oligomer | — |
| Experimental temperature | 160° C. |

TABLE 27-continued

MFR and MVR results for the blank sample

| Experiment No. | V153 (blank sample) |
|---|---|
| Preheating time | 4 min |
| Loading weight | 21.6 kg |
| MFR [g min] | 2.03 |
| MVR [cm³ min] | 1.50 |
| Density [g/cm³] | 1.349 |

TABLE 28

MFR and MVR results for experiments
V119, V120, V121, V122 and V123

| Experiment No. | V119 | V120 | V121 | V122 | V123 |
|---|---|---|---|---|---|
| Siloxane oligomer from | V092 | V093 | V094 | V095 | V096 |
| Experimental temperature: 160° C. | | | | | |
| Preheating time: 4 min | | | | | |
| Loading weight: 21.6 kg | | | | | |
| MFR [g min] | 3.22 | 3.69 | 3.63 | 3.55 | 3.50 |
| MVR [cm³ min] | 2.38 | 2.74 | 2.70 | 2.63 | 2.59 |
| Density [g/cm³] | 1.352 | 1.345 | 1.347 | 1.350 | 1.351 |

TABLE 29

MFR and MVR results for experiments V124, V125 and V126

| Experiment number | V124 | V125 | V126 |
|---|---|---|---|
| Siloxane oligomer from | V111 | V112 | V113 |
| Experimental temperature | | 160° C. | |
| Preheating time | | 4 min | |
| Loading weight | | 21.6 kg | |
| MFR [g min] | 3.84 | 3.69 | 3.77 |
| MVR [cm³ min] | 2.85 | 2.74 | 2.80 |
| Density [g/cm³] | 1.350 | 1.348 | 1.348 |

4.4 Water Uptake Capacity

Determination of water uptake: Test specimens of defined geometry are stored under defined conditions (temperature, time) in a water bath. The resulting change in weight of the samples is captured before and during storage and after the drying operations. The water uptake capacity was determined using the specimens produced, after a time period of 24 hours, by means of a triple determination, with the specimens having been stored in the water bath at 70° C. for the stated period.

TABLE 30

Results of the investigations into water uptake capacity

| PF experiment No. | Water uptake [mg/cm²]<br>after 7 d storage |
|---|---|
| V153 | 3.81 |
| V116 | 1.55 |
| V118 | 1.40 |
| V119 | 1.49 |
| V121 | 1.48 |
| V122 | 1.47 |
| V123 | 1.39 |
| V124 | 1.68 |
| V125 | 1.55 |
| V126 | 1.43 |

4.5 Determination of Tensile Properties

The tensile properties were determined in accordance with DIN EN ISO 527-1, 527-2, 527-3, the content of which is referenced in full and made part of the content of the present application. For this purpose, a sample rod of defined geometry is clamped into the tensile testing machine and subjected to uniaxial loading until breakage occurs (uniaxial extension at defined extension rate). The change in stress is recorded on the sample rod via the extension of the specimen, and the tensile strength and elongation at break are ascertained. Testing instrument: Zwick 4115 universal tester. By means of the specimens and tensile rods ("bones") produced, after 24 hours of storage in a conditioning chamber at 23° C. and 50% relative atmospheric humidity, the tensile properties (elongation at break and tensile strength) of the samples were determined, with a testing rate of 200 mm/min and a pre-tensioning force of 0.2 MPa, by means of a five-fold determination.

TABLE 31

Results from the investigations into tensile strength and elongation at break

| Siloxane oligomer from | PF experiment No. | Elongation at break [%] | Tensile strength [MPa] |
|---|---|---|---|
| V092 | V119 | 58.26 | 8.25 |
| V093 | V120 | 65.81 | 8.43 |
| V094 | V121 | 102.06 | 8.16 |
| V095 | V122 | 98.97 | 8.28 |
| V096 | V123 | 84.81 | 8.00 |
| V111 | V124 | 39.61 | 7.64 |
| V112 | V125 | 98.39 | 8.19 |
| V113 | V126 | 58.83 | 7.69 |
| V078 | V116 | 80.37 | 8.66 |
| V081 | V118 | 85.61 | 9.31 |

The invention claimed is:

1. A composition comprising an olefinically functionalized siloxane oligomer having not more than one olefinic radical on a silicon atom,
wherein:
the olefinically functionalized siloxane oligomer comprises Si-O-crosslinked structural elements that form a catenary, cyclic, crosslinked or optionally three-dimensionally crosslinked structure corresponding to a formula I,

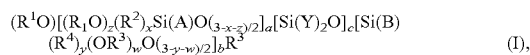

the structural elements are derived from one or more alkoxysilanes,
A corresponds to an olefinic radical and is a linear, branched or cyclic alkenyl- or cycloalkenyl-alkylene-functional group having in each case 2 to 16 C atoms,
B corresponds to a saturated hydrocarbon radical and is a linear, branched or cyclic alkyl radical having 1 to 16 C atoms,
Y corresponds to $OR^3$ or, in a crosslinked and optionally three-dimensionally crosslinked structure, independently of one another, to $OR^3$ or $O_{1/2}$,
$R^1$ independently at each occurrence corresponds to a linear, branched or cyclic alkyl radical having 1 to 4 C atoms or H,
$R^2$ corresponds independently at each occurrence to a linear, branched or cyclic alkyl radical having 1 to 15 C atoms,
$R^3$ independently at each occurrence corresponds to a linear, branched or cyclic alkyl radical having 1 to 4 C atoms or to H,
$R^4$ corresponds independently at each occurrence to a linear, branched or cyclic alkyl radical having 1 to 15 C atoms, a, b, c, x and y independently correspond to integers with $1 \leq a$, $0 \leq b$, $0 \leq c$, and $(a+b+c) \geq 2$,
z and x is 0 or 1,
y and w is 0 or 1,
a total chloride content in the composition is less than or equal to 250 mg/kg and
the structural elements $[R^1O)_{z(R^2)_x}Si(A)O_{(3-x-z)/2}]_a$, $[Si(B)(R^4)_y(OR^3)_wO_{(3-y-w)/2}]_b$ and $[Si(Y)_2O]_c$ in the formula I are present together, in relation to all silicon atoms of the formula I, at greater than or equal to 10% as a T structure,
wherein the olefinically functionalized siloxane oligomer is present at greater than or equal to 30% (area %, GPC) in relation to the overall composition with a molecular weight (Mw) of 500 to 700 g/mol in the composition.

2. The composition of claim 1, wherein the structural elements are derived from at least one selected from the group consisting of (i), (ii) and (iii),
(i) an olefinically functionalized alkoxysilane having a formula II,

where A corresponds to an olefinic radical and is a linear, branched or cyclic alkenyl-or cycloalkenyl-alkylene-functional group having in each case 2 to 16 C atoms, $R^2$ independently at each occurrence is a linear, branched or cyclic alkyl radical having 1 to 15 C atoms, x is 0 or 1, z' is 2 or 3 and $R^1$ independently corresponds to a methyl, ethyl or propyl group,
(ii) an alkoxysilane of a formula III functionalized with a saturated hydrocarbon radical,

where B corresponds to an unsubstituted hydrocarbon radical and is a linear, branched or cyclic alkyl radical having 1 to 16 C atoms, $R^4$ independently at each occurrence is a linear, branched or cyclic alkyl radical having 1 to 15 C atoms, y is 0 or 1, w' is 2 or 3 and $R^3$ independently corresponds to a methyl, ethyl or propyl group, and
(iii) a tetraalkoxysilane of a formula IV

where $R^3$ independently at each occurrence is a methyl, ethyl or propyl group.

3. The composition of claim 1, wherein one or more of conditions (i), (ii), (iii), (iv) and (v) is satisfied:
(i) the structural element $[(R^1O)_z(R^2)_xSi(A)O_{(3-x-z)/2}]_a$ in the formula I is present, in relation to all silicon atoms of the formula I, at greater than or equal to 5%, as a T structure,
(ii) the structural elements $[(R^1O)_z(R^2)_xSi(A)O_{(3-x-z)/2}]_a$ and $[Si(B)(R^4)_y(OR^3)_wO_{(3-y-w)/2}]_b$ and $[Si(Y)_2O]_c$ in the formula I are present together, in relation to all silicon atoms of the formula I, at greater than or equal to 50% as a D structure,
(iii) the structural element $[(R^1O)_z(R^2)_xSi(A)O_{(3-x-z)/2}]_a$ is present in the formula I, in relation to all silicon atoms of the formula I, at less than or equal to 35% as an M structure,
(iv) the structural element $[Si(B)(R^4)_y(OR^3)_wO_{(3-y-w)/2}]_b$ in the formula I is present, in relation to all silicon atoms of the formula I, at less than or equal to 25% as an M structure, and
(v) the structural element $[Si(Y)_2O]_c$ in the formula I is present at greater than or equal to 20% as a D structure, or more than 40% of the structural elements $[Si(Y)_2O]_c$ in the formula I are present as D structure.

4. The composition of claim 2, wherein:
in the olefinically functionalized alkoxysilane of the formula II, x is 0 and,
optionally, in the alkoxysilane of the formula III functionalized with a saturated hydrocarbon radical, y is 0.

5. The composition of claim 2, wherein:
in formulae I and/or II, the olefinic radical A is a non-hydrolyzable olefinic radical selected from the group consisting of vinyl, allyl butenyl, 3-butenyl, pentenyl, hexenyl, ethylhexenyl, heptenyl, octenyl, cyclohexenyl-C1 to C8-alkylene, cyclohexenyl-2-ethylene, 3'-cyclohexenyl-2-ethylene, cyclohexadienyl-C1 to C8-alkylene, and cyclohexadienyl-2-ethylene, and independently thereof
in formulae I and/or III, the unsubstituted hydrocarbon radical B is selected from the group consisting of methyl, ethyl, propyl, butyl, isobutyl, n-butyl, tert-butyl, pentyl, n-pentyl, isopentyl, neopentyl, hexyl, isohexyl, neohexyl, 2,2-dimethylbutyl, 2,3-dimethylbutyl, 2-methylpentyl, 3-methylpentyl, heptyl, octyl, n-octyl, isooctyl, nonyl, decyl, undecyl, dodecyl, $C_{13}H_{27}$, $C_{14}H_{29}$, $C_{15}H_{31}$ and hexadecyl, and
independently at each occurrence $R^1$ is a methyl, ethyl or propyl group and $R^3$ independently is a methyl, ethyl or propyl group.

6. The composition of claim 2, wherein:
in formulae I and/or II, the olefinic radical A is a vinyl group, and independently thereof
in formulae I and/or III, the unsubstituted hydrocarbon radical B is selected from the group consisting of methyl, ethyl, propyl, butyl, isobutyl, n-butyl, tert-butyl, pentyl, n-pentyl, isopentyl, neopentyl, hexyl, isohexyl, neohexyl, 2,2-dimethylbutyl, 2,3-dimethylbutyl, 2-methylpentyl, 3-methylpentyl, heptyl, octyl, n-octyl, isooctyl, nonyl, decyl, undecyl, dodecyl, $C_{13}H_{27}$, $C_{14}H_{29}$, $C_{15}H_{31}$ and hexadecyl, and
independently at each occurrence $R^1$ is a methyl, ethyl or propyl group and $R^3$ independently is a methyl, ethyl or propyl group.

7. The composition of claim 1, wherein the olefinically functionalized siloxane oligomer comprises at least two siloxanes selected from the group consisting of trisiloxane, tetrasiloxane, pentasiloxane, cyclotetrasiloxane, cyclopentasiloxane and cyclohexasiloxane, wherein the oligomer is present in an amount of at least 60% of the composition.

8. The composition of claim 1, wherein a mass loss of 50 wt %, determined by TGA, occurs at a temperature above 240° C.

9. The composition of claim 1, wherein a loss of mass by the composition as determined by TGA, using a platinum crucible, a lid with hole, at 10 K/min, at a temperature up to and including 150° C. is less than 5 wt %.

10. The composition of claim 1, wherein a loss of mass by the composition as determined by TGA, using a platinum crucible, a lid with hole, at 10 K/min, at a temperature up to and including 200° C. is less than 20 wt %.

11. The composition of claim 1, wherein an alcohol content after complete hydrolysis of the hydrolyzable alkoxy groups is less than or equal to 20 wt %.

12. The composition of claim 2, wherein:
(i) a ratio of the silicon atoms selected from silicon atoms functionalized olefinically and silicon atoms functionalized with a saturated hydrocarbon to alkoxy groups in the siloxane oligomer is from 1:0.3 to 1:2.0, with the proviso that the olefinically functionalized siloxane oligomer derives from alkoxysilanes of the formulae II and III, or (ii) a ratio of the silicon atoms selected from silicon atoms functionalized olefinically and silicon atoms functionalized with a saturated hydrocarbon to alkoxy groups in the siloxane oligomer is from 1:0.9 to 1:2.5, with the proviso that the olefinically functionalized siloxane oligomer derives from alkoxysilanes of the general formulae II and IV and of the formula III.

13. The composition of claim 2, wherein an amount of silicon atoms in monomeric alkoxysilanes therein is less than or equal to 3% to 0.0% in relation to all silicon atoms, with monomeric alkoxysilanes being considered to be the alkoxysilanes of the formulae II, III and/or IV and also their monomeric hydrolysis products.

14. The composition of claim 2, wherein:
a) the siloxane oligomer and at least one structure of the formula I, in each case derived from the alkoxysilane of the formula II, have a vinyl group as olefinic radical A, with $R^1$ independently at each occurrence corresponding to a methyl or ethyl group,
b) the siloxane oligomer and at least one structure of the formula I, in each case derived from the alkoxysilane of the formula II, have a vinyl group as olefinic radical A, and derived from the alkoxysilane of the formula III have a propyl group as unsubstituted hydrocarbon radical B, where $R^1$ and $R^3$ independently at each occurrence correspond to a methyl or ethyl group, or
c) the siloxane oligomer and at least one structure of the formula I, in each case derived from the alkoxysilane of the formula II and formula IV and optionally of the formula III, are selected from a) or b), where $R^3$ derives from formula IV and independently at each occurrence corresponds to a methyl or ethyl group.

15. The composition of claim 2 wherein, in each case independently, the siloxane oligomer comprises at least one structural element selected from the group consisting of vinyltriethoxysilane, vinyltrimethoxysilane, methyltriethoxysilane, methyltrimethoxysilane, ethyltriethoxysilane, ethyltrimethoxysilane, propyltriethoxysilane, propyltrimethoxysilane, butyltriethoxysilane, butyltrimethoxysilane, n-butyltriethoxysilane, n-butyltrimethoxysilane, isobutyltriethoxysilane, isobutyltrimethoxysilane, hexyltriethoxysilane, hexyltrimethoxysilane, n-hexyltriethoxysilane, n-hexyltrimethoxysilane, isohexyltriethoxysilane, isohexyltrimethoxysilane, heptyltriethoxysilane, heptyltrimethoxysilane, octyltriethoxysilane, octyltrimethoxysilane, n-octyltriethoxysilane, n-octyltrimethoxysilane, isooctyltriethoxysilane, isooctyltrimethoxysilane, undecyltriethoxysilane, undecyltrimethoxysilane, decyltriethoxysilane, decyltrimethoxysilane, nonadecyltriethoxysilane, nonadecyltrimethoxysilane, dodecyltriethoxysilane, dodecyltrimethoxysilane, $C_{13}H_{27}$-triethoxysilane, $C_{13}H_{27}$-trimethoxysilane, $C_{14}H_{29}$-triethoxysilane, $C_{14}H_{29}$-trimethoxysilane, $C_{15}H_{31}$-trimethoxysilane, $C_{15}H_{31}$-triethoxysilane, hexadecyltriethoxysilane, hexadecyltrimethoxysilane, and any transesterification product thereof.

16. A composition comprising an olefinically functionalized siloxane oligomer having not more than one olefinic radical on a silicon atom,
wherein:
the olefinically functionalized siloxane oligomer comprises Si-O-crosslinked structural elements that form a catenary, cyclic, crosslinked or optionally three-dimensionally crosslinked structure corresponding to a formula I,

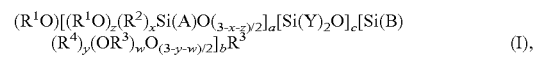

(I), the structural elements are derived from one or more alkoxysilanes,

A corresponds to an olefinic radical and is a linear, branched or cyclic alkenyl- or cycloalkenyl-alkylene-functional group having in each case 2 to 16 C atoms, B corresponds to a saturated hydrocarbon radical and is a linear, branched or cyclic alkyl radical having 1 to 16 C atoms, Y corresponds to $OR^3$ or, in a crosslinked and optionally three-dimensionally crosslinked structure, independently of one another, to $OR^3$ or $O_{1/2}$, $R^1$ independently at each occurrence corresponds to a linear, branched or cyclic alkyl radical having 1 to 4 C atoms or H, $R^2$ corresponds independently at each occurrence to a linear, branched or cyclic alkyl radical having 1 to 15 C atoms, $R^3$ independently at each occurrence corresponds to a linear, branched or cyclic alkyl radical having 1 to 4 C atoms or to H, $R^4$ corresponds independently at each occurrence to a linear, branched or cyclic alkyl radical having 1 to 15 C atoms, a, b, c, x and y independently correspond to integers with $1 \le a$, $0 \le b$, $0 \le c$, and $(a+b+c) \ge 2$, z and x is 0 or 1, y and w is 0 or 1, a total chloride content in the composition is less than or equal to 250 mg/kg and the structural elements $[(R^1O)_z(R^2)_xSi(A)O_{(3-x-z)/2}]_a$, $[Si(B)(R^4)_y(OR^3)_wO_{(3-y-w)/2}]_b$ and $[Si(Y)_2O]_c$ in the formula I are present together, in relation to all silicon atoms of the formula I, at greater than or equal to 10% as a T structure, wherein the composition has a weight-average molecular weight of 564 to 1083 g/mol.

17. A process for preparing the composition of claim 1, the process comprising reacting:

(i) an olefinically functionalized alkoxysilane of formula II,

where in formula II A corresponds to an olefinic radical and is a linear, branched or cyclic alkenyl- or cycloalkenyl-alkylene-functional group having in each case 2 to 16 C atoms, $R^2$ independently corresponds to a linear, branched or cyclic alkyl radical having 1 to 15 C atoms, x is 0 or 1, z' is 2 or 3, and $R^1$ independently corresponds to a linear, branched or cyclic alkyl radical having 1 to 4 C atoms, (ii) in the presence of at least one of a hydrolysis catalyst and a condensation catalyst (iii) with an amount of water of 1.1 to 1.59 mol of water per mole of silicon atoms in the alkoxysilanes used, optionally in the presence of a solvent, to obtain a siloxane oligomer, and (iv) substantially removing the hydrolysis alcohol and the solvent that is optionally present, and (v) setting a total chloride content in the composition of less than or equal to 250 mg/kg, (vi) where greater than or equal to 10% of the silicon atoms in the olefinically functionalized siloxane oligomer, in relation to the sum total of silicon atoms in the siloxane oligomer, are present as a T structure, and (vii) where the composition is obtained as liquid-phase product, wherein the amount of water is metered in continuously or with at least one interruption over a period of 1 to 1000 minutes and the temperature in the reaction mixture is 5 to 90° C., at a pH of less than or equal to 7, the water being added optionally together with the catalyst and/or with an alcohol, and the reaction mixture is optionally reacted further for at least 10 minutes to 36 hours at 5 to 80° C.

18. The process of claim 17, further comprising reacting the olefinically functionalized alkoxysilane of the formula II, in the presence of a hydrolysis and/or condensation catalyst, with (i.1) at least one alkoxysilane of formula III,

where in formula III B corresponds to a saturated hydrocarbon radical and is a linear, branched or cyclic alkyl radical having 1 to 16 C atoms, $R^3$ corresponds independently at each occurrence to a linear, branched or cyclic alkyl radical having 1 to 4 C atoms, $R^4$ corresponds to a linear, branched or cyclic alkyl radical having 1 to 15 C atoms, y is 0 or 1, and w' is 2 or 3.

19. The process of claim 17, further comprising reacting the olefinically functionalized alkoxysilane of the formula II, in the presence of a hydrolysis and/or condensation catalyst, with (i.2) at least one tetraalkoxysilane of formula IV,

where in formula IV $R^3$ independently at each occurrence is a linear, branched or cyclic alkyl radical having 1 to 4 C atoms.

20. The process of claim 17, wherein an alcohol solvent is present in (iii).

21. The process of claim 17, wherein:

in the olefinically functionalized alkoxysilane of the formula II

A is a vinyl, allyl, butenyl, pentenyl, hexenyl, ethylhexenyl, heptenyl, octenyl, cyclohexenyl-C1 to C8-alkylene, cyclohexenyl-2-ethylene, 3'-cyclohexenyl-26-ethylene, cyclohexadienyl-C1 to C8-alkylene or cyclohexadienyl-2-ethylene group, x is 0 or 1, z' is 2 or 3 $R^2$ independently corresponds to a linear, branched or cyclic alkyl radical having 1 to 15 C atoms, and $R^1$ independently is a methyl, ethyl or propyl group, and independently optionally in the alkoxysilane of the formula III

the unsubstituted hydrocarbon radical B is a methyl, ethyl, propyl, butyl, isobutyl, n-butyl, tert-butyl, pentyl, n-pentyl, isopentyl, neopentyl, hexyl, isohexyl, neohexyl, 2,2-dimethylbutyl, 2,3-dimethylbutyl, 2-methylpentyl, 3-methylpentyl, heptyl, octyl, n-octyl, isooctyl, nonyl, decyl, undecyl, dodecyl, $C_{13}H_{27}$, $C_{14}H_{29}$, $C_{15}H_{31}$ or hexadecyl group, y is 0 or 1, w' is 2 or 3 $R^4$ corresponds to a linear, branched or cyclic alkyl radical having 1 to 15 C atoms, and $R^3$ independently is a methyl, ethyl or propyl group.

22. The process of claim 18 wherein, in the olefinically functionalized alkoxysilane of the formula II, x is 0, and/or, in the alkoxysilane of the formula III functionalized with a saturated hydrocarbon radical, y is 0.

23. The process of claim 18, wherein
the olefinically functionalized alkoxysilane of the formula II is selected from the group consisting of vinyltriethoxysilane, allyltriethoxysilane, butenyltriethoxysilane, pentenyltriethoxysilane, hexenyltriethoxysilane, ethylhexenyltriethoxysilane, heptenyltriethoxysilane, octenyltriethoxysilane, cyclohexenyl-C1 to C8-alkylenetriethoxysilane, cyclohexenyl-2-ethylenetriethoxysilane, 3'-cyclohexenyl-2-ethylenetriethoxysilane, cyclohexadienyl-C1 to C8-alkylenetriethoxysilane, cyclohexadienyl-2-ethylenetriethoxysilane, vinyltrimethoxysilane, allyltrimethoxysilane, butenyltrimethoxysilane, pentenyltrimethoxysilane, hexenyltrimethoxysilane, ethylhexenyltrimethoxysilane, heptenyltrimethoxysilane, octenyltrimethoxysilane, cyclohexenyl-C1 to C8-alkylenetrimethoxysilane, cyclohexenyl-2-ethylenetrimethoxysilane, 3'-cyclohexenyl-2-ethylenetrimethoxysilane, cyclohexadienyl-C1 to C8-allcylenetrimethoxysilane and cyclohexadienyl-2-ethylenetrimethoxysilane, and, in each case independently,
the alkoxysilane of the formula III is selected from the group consisting of methyltriethoxysilane, ethyltriethoxysilane, n-propyltriethoxysilane, isopropyltriethoxysilane, butyltriethoxysilane, n-butyltriethoxysilane, isobutyltriethoxysilane, hexyltriethoxysilane, n-hexyltriethoxysilane, isohexyltriethoxysilane, heptyltriethoxysilane, octyltriethoxysilane, n-octyltriethoxysilane, isooctyltriethoxysilane, undecyltriethoxysilane, decyltriethoxysilane, nonadecyltriethoxysilane, dodecyltriethoxysilane, $C_{13}H_{27}$-triethoxysilane, $C_{14}H_{29}$-triethoxysilane or $C_{15}H_{31}$-triethoxysilane, hexadecyltriethoxysilane, methyltrimethoxysilane, ethyltrimethoxysilane, n-propyltrimethoxysilane, isopropyltrimethoxysilane, butyltrimethoxysilane, n-butyltrimethoxysilane, isobutyltrimethoxysilane, hexyltrimethoxysilane, n-hexyltrimethoxysilane, isohexyltrimethoxysilane, heptyltrimethoxysilane, octyltrimethoxysilane, n-octyltrimethoxysilane, isooctyltrimethoxysilane, undecyltrimethoxysilane, decyltrimethoxysilane, nonadecyltrimethoxysilane, dodecyltrimethoxysilane, $C_{13}H_{27}$-trimethoxysilane, $C_{14}H_{29}$-trimethoxysilane or $C_{15}H_{31}$-trimethoxysilane and hexadecyltrimethoxysilane.

24. The process of claim 17, wherein a defined amount of water of 1.1 to 1.58 mol of water per mole of silicon atoms in the alkoxysilanes of the formula II and/or III is added.

25. The process of claim 24, wherein a defined amount of water of 1.2 to 1.57 mol per mole of silicon atoms in the alkoxysilanes of the formula II and/or III is added.

26. The process of claim 17, wherein the catalyst is an acidic catalyst.

27. The process of claim 17, wherein the alcohol is substantially completely removed.

28. The process of claim 17, wherein the hydrolysis alcohol and the solvent optionally present are removed by distillation.

29. The process of claim 18, wherein the silane of the formula II and the silane of the formula III are used in a ratio of 1:0 to 1:8.

30. The composition of claim 16, wherein the structural elements are derived from at least one selected from the group consisting of (i), (ii) and (iii),
(i) an olefinically functionalized alkoxysilane having a formula II, $$A\text{-}Si(R^2)_x(OR^1)_{z'} \quad (II)$$

where A corresponds to an olefinic radical and is a linear, branched or cyclic alkenyl-or cycloalkenyl-alkylene-functional group having in each case 2 to 16 C atoms, $R^2$ independently at each occurrence is a linear, branched or cyclic alkyl radical having 1 to 15 C atoms, x is 0 or 1, z' is 2 or 3 and $R^1$ independently corresponds to a methyl, ethyl or propyl group,
(ii) an alkoxysilane of a formula III functionalized with a saturated hydrocarbon radical, $$B\text{—}Si(R^4)_y(OR^3)_{w'} \quad (III)$$

where B corresponds to an unsubstituted hydrocarbon radical and is a linear, branched or cyclic alkyl radical having 1 to 16 C atoms, $R^4$ independently at each occurrence is a linear, branched or cyclic alkyl radical having 1 to 15 C atoms, y is 0 or 1, w' is 2 or 3 and $R^3$ independently corresponds to a methyl, ethyl or propyl group, and
(iii) a tetraalkoxysilane of a formula IV $$Si(OR^3)_4 \quad (IV)$$

where $R^3$ independently at each occurrence is a methyl, ethyl or propyl group.

31. The composition of claim 16, wherein a mass loss of 50 wt %, determined by TGA, occurs at a temperature above 240° C.

32. The composition of claim 16, wherein a loss of mass by the composition as determined by TGA, using a platinum crucible, a lid with hole, at 10 K/min, at a temperature up to and including 150° C. is less than 5 wt %.

33. The composition of claim 16, wherein a loss of mass by the composition as determined by TGA, using a platinum crucible, a lid with hole, at 10 K/min, at a temperature up to and including 200° C. is less than 20 wt %.

34. The composition of claim 16, wherein an alcohol content after complete hydrolysis of the hydrolyzable alkoxy groups is less than or equal to 20 wt %.

35. A process for preparing the composition of claim 16, the process comprising reacting:
(i) an olefinically functionalized alkoxysilane of formula II, $$A\text{-}Si(R^2)_x(OR^1)_{z'} \quad (II),$$

where in formula II A corresponds to an olefinic radical and is a linear, branched or cyclic alkenyl- or cycloalkenyl-alkylene-functional group having in each case 2 to 16 C atoms, $R^2$ independently corresponds to a linear, branched or cyclic alkyl radical having 1 to 15 C atoms, x is 0 or 1, z' is 2 or 3, and $R^1$ independently corresponds to a linear, branched or cyclic alkyl radical having 1 to 4 C atoms,
(ii) in the presence of at least one of a hydrolysis catalyst and a condensation catalyst
(iii) with an amount of water of 1.1 to 1.59 mol of water per mole of silicon atoms in the alkoxysilanes used, optionally in the presence of a solvent, to obtain a siloxane oligomer, and
(iv) substantially removing the hydrolysis alcohol and the solvent that is optionally present, and
(v) setting a total chloride content in the composition of less than or equal to 250 mg/kg,
(vi) where greater than or equal to 10% of the silicon atoms in the olefinically functionalized siloxane oligomer, in relation to the sum total of silicon atoms in the siloxane oligomer, are present as a T structure, and
(vii) where the composition is obtained as liquid-phase product,
wherein the amount of water is metered in continuously or with at least one interruption over a period of 1 to 1000 minutes and the temperature in the reaction mixture is 5 to 90° C., at a pH of less than or equal to 7, the water being added optionally together with the catalyst and/or with an alcohol, and the reaction mixture is optionally reacted further for at least 10 minutes to 36 hours at 5 to 80° C.

* * * * *